(12) United States Patent
Groves et al.

(10) Patent No.: US 8,114,602 B2
(45) Date of Patent: Feb. 14, 2012

(54) DETECTION OF MOLECULAR INTERACTIONS

(75) Inventors: John T. Groves, Berkeley, CA (US); Michael M. Baksh, Fremont, CA (US); Michal Jaros, Brno (CH)

(73) Assignee: The Regents of the University of California, Oakland, CA (US)

(*) Notice: Subject to any disclaimer, the term of this patent is extended or adjusted under 35 U.S.C. 154(b) by 665 days.

(21) Appl. No.: 10/581,371

(22) PCT Filed: Dec. 6, 2004

(86) PCT No.: PCT/US2004/040872
§ 371 (c)(1),
(2), (4) Date: Apr. 19, 2007

(87) PCT Pub. No.: WO2005/106047
PCT Pub. Date: Nov. 10, 2005

(65) Prior Publication Data
US 2007/0275369 A1    Nov. 29, 2007

Related U.S. Application Data

(60) Provisional application No. 60/527,209, filed on Dec. 4, 2003.

(51) Int. Cl.
*G01N 33/53* (2006.01)
*C12Q 1/70* (2006.01)
*B01F 3/12* (2006.01)

(52) U.S. Cl. .......................... 435/7.1; 516/77; 435/5

(58) Field of Classification Search .................. None
See application file for complete search history.

(56) References Cited

U.S. PATENT DOCUMENTS

| | | | | |
|---|---|---|---|---|
| 4,240,751 A | * | 12/1980 | Linnecke et al. | 356/409 |
| 4,410,660 A | * | 10/1983 | Straus | 525/54.1 |
| 2002/0034827 A1 | * | 3/2002 | Singh et al. | 436/177 |

FOREIGN PATENT DOCUMENTS

| WO | WO 03/098183 | 12/2001 |
|---|---|---|
| WO | WO 03/098183 A | 11/2003 |

OTHER PUBLICATIONS

Tang, et al. Colloidal nanoparticles from Poly(N-isopropylacrylamide)-graft-DNA for single nucleotide. Chem. Lett. 2004; 33(12): 1602-1603.*

Schaertl, et al. A novel and Robust Homogeneous Gluorescence-Based Assay Using Noanoparticles for Pharmaceutical Screening and Diagnostics. J. Biomel. Screen. 2000; 5(4): 227-237.*

(Continued)

*Primary Examiner* — Zachariah Lucas
*Assistant Examiner* — Stuart W Snyder
(74) *Attorney, Agent, or Firm* — Knobbe Martens Olson & Bear LLP

(57) ABSTRACT

A method and assay are described for measuring the interaction between a ligand and an analyte. The assay can include a suspension of colloidal particles that are associated with a ligand of interest. The colloidal particles are maintained in the suspension at or near a phase transition state from a condensed phase to a dispersed phase. An analyte to be tested is then added to the suspension. If the analyte binds to the ligand, a phase change occurs to indicate that the binding was successful.

50 Claims, 15 Drawing Sheets

OTHER PUBLICATIONS

Faulds, et al. Assessment of silver and gold substrates for the detection of amphetamine sulfate by surface enhanced Raman scattering (SERS). Analyst. 2002; 127:282-286.*

University of California Berkeley, *Phase transitions and molecular detection in a lipid membrane derivatized silica colloid*, Retrieved from the Internet: URL: http://web.archive.org/web/20041106102410/http://www.nst1.org/nanotech2003/showabstract.html?absno=775>, (Feb. 25, 2003) [retrieved on Feb. 15, 2008] Date of Oral Disclosure: Feb. 25, 2008, Date of online publication of the written report: Jun. 11, 2004, abstract, & Nano Science and Technology Institute: "Nanotech 2003 Technical Program—Tuesday Feb. 25" [online] Sep. 1, 2004, XP002469190 Retrieved from the internet: URLhttp://web.archive.org/web/20040901085055/http://www.nsti.org/Nanotech2003/tuesday.html> [retrieved on Feb. 15, 2008].

Bosma et al., *Preparation of monodisperse, fluorescent PMMA-latex colloids by dispersion polymerization*, Journal of Colloid and Interface Science, vol. 245 No. 2, pp. 292-300 (Jan. 2002).

Baksh et al., *Detection of molecular interactions at membrane surfaces through colloid phase transitions*, Nature (London), vol. 427 No. 6970, pp. 139-141 (Jan. 2004).

Dluzewski et al., *Origins of the parasitophorous vacuole membrane of the malaria parasite, Plasmodium falciparum, in human red blood cells*, Journal of Cell Science, vol. 102 Pt. 3, pp. 527-532 (Jul. 1992).

Buranda et al., *Biomimetic molecular assemblies on glass and mesoporous silica microbeads for biotechnology*, Langmuir, vol. 19 No. 5, pp. 1654-1663, (Mar. 2003).

Loidl-Stahlhofen et al., *Solid-Supported Biomolecules on Modified Silica Surfaces—A Tool for Fast Physicochemical Characterization and High-throughput Screening*, Advanced Materials, vol. 13 No. 23, pp. 1829-1834, (Dec. 2001).

Tang et al., *Single Nucleotide Polymorphisms (SNPS) Assay Using Reversible Association and Dispersion of DNA-Linked Colloidal Nanoparticles*, Nucleic Acids Symposium Series, vol. 1 No. 1, pp. 165-166, (2001).

Winter et al., *Surface binding affinity measurement from order transitions of lipid membrane-coated colloidal particles*, Analytical Chemistry, vol. 78 No. 1, pp. 174-180 (Jan. 2006).

University of California Berkeley, US: Phase transitions and molecular detection in a lipid membrane derivatized silica colloid. [Online] Feb. 25, 2003.

Baksh, M.M. et al. (2004) Detection of molecular interactions at membrane surfaces through colloid phase transitions. Nature. 427:139-141.

Bosma, G. et al. (2002) Preparation of monodisperse, fluorescent PMMA-Latex colloids by dispersion polymerization. Journal of Colloid and Interface Science. 245:292-300.

Dluzewski, A.R. et al. (1992) Origins of the parasitophorous vacuole membrane of the malaria parasite, *Plasmodium falciparum*, in human red blood cells. Journal of Cell Science. 102:527-532.

Loidl-Stahlhofen, A. et al. (2001) Solid-supported biomolecules on modified silica surfaces—a tool for fast physicochemical characterization and high-throughput screening. Adv. Mater. 13(23):1829-1834.

Winter, E.M. et al. (2006) Surface binding affinity measurements from order transitions of lipid membrane-coated colloidal particles. Anal. Chem. 78:174-180.

Anderson et al. *Nature*. 416:811-816 (2002).

Bayerl et al. *Biophys. J.* 58:357-362 (1990).

Buranda et al. *Langmuir*. 19:1654-1663 (2003).

Discher et al. *Science*. 297:967-973 (2002).

Fang et al. *J. Am. Chem. Soc.* 124(11):2394-2395 (2002).

Grakoui et al. *Science*. 285: 221-227 (1999).

Groves et al. *Biophys. J.* 71:2716-2723 (1996).

Groves, J. T. *Curr. Op. Drug Disc. & Dev.* 5:606-612 (2002).

Hoffman et al. *Proc. Natl. Acad. Sci. USA*. 97:11215-11220 (2000).

Kunneke et al. *Angew. Chem. Int. Ed.* 41(2):314-316 (2002).

Mbamala et al. *Physical Review*. 67:031608-01-10 (2003).

Sackmann, E. *Science*. 271:43-48 (1996).

Salafsky et al. *Biochemistry*. 35:14773-14781 (1996).

Tanaka et al. *J. Am. Chem. Soc.* 126:3257-3260 (2004).

Tang et al. *Nucleic Acids Research*. Supp. 1:165-166 (2001).

Wong and Groves. *Proc. Natl. Acad. Sci. USA*. 99:14147 (2002).

Yang et al. *Analytical Chemistry*. 73(2):165-169 (2001).

Yethira et al. *Nature*. 421:513-517 (2003).

Zollner et al. (2003) Adsorption of isotype "E" antibodies on affinity magnetoliposomes. Journal of Dispersion Science and Technology. 24(3&4):615-622.

* cited by examiner

No Ganglioside Membrane

FIGURE 5c

$G_{M1}$-Containing Membrane

FIGURE 5d

$G_{T1B}$-Containing Membrane

FIGURE 5e a b

DETECTION OF MOLECULAR INTERACTIONS

RELATED APPLICATIONS

The application is a U.S. national phase application under 35 U.S.C. §371 of International Application No. PCT/US2004/040872, filed on Dec. 6, 2004, by Groves et al., entitled "DETECTION OF MOLECULAR INTERACTIONS," which claims priority to U.S. provisional Application No. 60/527,209, filed Dec. 4, 2003 by Groves et al., both of which are incorporated herein by reference in their entireties.

STATEMENT OF GOVERNMENTAL SUPPORT

This invention was made during work supported by the U.S. Department of Energy at Lawrence Berkeley National Laboratory under contract No. DE-AC03-76SF00098. The government has certain rights in this invention.

BACKGROUND OF THE INVENTION

1. Field of the Invention

The present invention relates to compositions and methods for assaying binding interactions between an analyte of interest and a ligand of interest. More specifically, the invention relates to detecting interactions of analytes and ligands by observing changes in the collective behavior of colloidal particles in solution.

2. Description of the Related Art

Most biomolecules interact with other biomolecules in order to carry out their functions in vivo. For example, cellular processes often involve proteins bound together in multisubunit complexes. In addition, interactions between multiple types of biomolecules create a diversity of cellular structures, such as the cytoskeleton and cellular membranes. Moreover, many pathogens, diseases, and physiologically significant conditions can be diagnosed by the presence of particular substances within a biological sample. Accordingly, there is a general need for sensitive, low-cost methods of detecting binding between analytes and ligands of interest.

Some ligands naturally reside within cellular membranes. For this reason, cellular membranes have been extensively studied to determine a linkage between those ligands and their functions in vivo. For example, many known therapeutic drugs target biomolecules, such as receptors, that reside on the surface of cellular membranes. A significant challenge in studying biochemical reactions on membrane surfaces is the difficulty in emulating the naturally fluid membrane environment within an in vitro assay. One strategy involves coating solid substrates, such as silica or certain polymers with lipid membranes in order to emulate the structure of cell membranes in vivo (Sackmann, E., Science 271: 43-48 (1996); Groves, J. T., Curr. Op. Drug Disc. & Dev., 5: 606-612 (2002)). Using this technology, membranes were firmly trapped near the solid interface, but also retained their natural fluidity and biological functionality (Grakoui et al., Science 285: 221-227 (1999)).

Lipid membranes floating on a supported surface, such as silica, have been used to study a variety of therapeutically valuable membrane proteins, including G protein-coupled receptors (Fang et al., J. Am. Chem. Soc., 124: 2394-2395 (2002)). However, detection of molecular interactions on those membrane surfaces generally required elaborate techniques such as surface plasmon resonance (SPR) (e.g., Hoffman et al., Proc. Natl. Acad. Sci. USA, 97: 11215-11220 (2000)) or total internal reflection (TIR) microscopy (Yang et al., Anal. Chem., 73:165-169 (2001)). These techniques normally necessitate the use of fluorescent labels.

SUMMARY OF THE INVENTION

Embodiments of the invention relate to methods and compositions for detecting binding events between an analyte and a ligand by observing the collective behavior of a population of colloidal particles. In various embodiments, the invention includes methods for detecting and characterizing binding between an analyte and a ligand, colloidal particles useful for detecting such binding and methods of preparing the colloidal particles. Other embodiments include kits for detecting and characterizing molecular binding interactions.

In one embodiment, a ligand of interest is associated directly or indirectly with the surface of colloidal particles to create a population of modified colloids. The modified colloids are then incubated under conditions that allow them to achieve an equilibrium or near-equilibrium distribution in an aqueous solution. The colloids preferably exhibit free lateral diffusion, and the system preferably exhibits the characteristics of an ergodic fluid. In some embodiments, the modified colloids settle gravitationally onto an underlying substrate and form a two-dimensional colloid. The distribution of the colloidal particles is preferably measured using direct optical imaging, in connection with a computer-aided analysis.

To detect whether an analyte of interest binds to the modified colloids, the analyte is added to the colloidal solution. The analyte may be added in its free form, or may be associated with other materials or structures, such as a live cell. Binding can be detected by observing changes in the distribution of the modified colloidal particles at or near equilibrium upon addition of the analyte. In some embodiments, binding induces a phase transition among the particles from a condensed phase to a dispersed phase. In other embodiments, the addition of analyte results in a phase transition from a dispersed phase to a condensed phase. In yet further embodiments, binding can be measured by changes in the distribution of the colloidal particles without the particles undergoing a defined phase transition.

The distribution of colloidal particles can be viewed using direct optical imaging. Phase transitions can also be detected using the naked eye or a device that measures the spatial distribution of the particles in solution. In some embodiments, phase transitions are determined by performing a statistical analysis of particle pair distribution functions, enabling a quantitative comparison of the modified colloidal distribution in the presence and absence of the analyte. In other embodiments, different statistical analyses are utilized to describe differences in colloidal phase behavior.

The colloidal particles may be of any size and/or composition. In some embodiments, the colloidal particles are substantially spherical colloidal particles formed from porous or nonporous materials, such as silica. In one aspect of the invention, the colloidal particles are derivatized with a lipid membrane layer. The lipid layer may be a bilayer, a monolayer, or other structure. The lipid membrane layer can be doped or derivatized with a ligand specific for an analyte in order to create a modified particle. In one aspect, derivatized particles having an outer doped lipid membrane layer with a water layer between the doped lipid layer and the particle surface are used. In one embodiment, the lipid membrane is doped with a cell-surface protein or membrane-associated ligand. In this embodiment, analyte binding to the membrane surfaces through the ligand results in the particles undergoing a phase transition from a condensed to dispersed population.

Embodiments of the invention are useful for identifying and characterizing binding interactions between ligands and analytes. For example, in one embodiment, membrane-derivatized colloidal particles are used to investigate analyte interactions with cell surface molecules within a lipid bilayer environment. In another embodiment, such modified colloidal populations are used as a diagnostic tool to detect the presence of analytes associated with diseases, pathogens, drugs, or various physiological states. For example, membrane-targeting bacterial toxins (e.g. botulism, cholera, anthrax, tetanus) and viruses can be diagnosed by detecting binding to their lipid ligands.

These and other objects and features of the invention will become more fully apparent when the following detailed description is read in conjunction with the accompanying drawings.

BRIEF DESCRIPTION OF THE DRAWINGS

FIG. 2a is a photograph that shows the two-dimensional Brownian trajectories of membrane-derivatized particles, which have settled gravitationally to the bottom of a dish filled with water. FIG. 2b is a set of four photographs that show a time sequence of images of a condensed phase of the colloid illustrating the mobility of individual particles into and out of condensed crystallites. The time sequence is taken at t=0, t=90 seconds, t=180 seconds and t=270 seconds.

FIG. 3a is a set of four photographs that show a time sequence of images depicting the transition from a condensed to a dispersed colloidal phase, triggered by addition of protein. Photographs were taken at time t=0, t=30 seconds, t=60 seconds and t=240 seconds. FIG. 3b is a three-dimensional graph g(r) for the time sequence shown in FIG. 3a.

FIG. 4a is a plot of measured g(r) functions for dispersions of particles (area fraction $\phi$=0.15) derivatized with fluid membranes (90% DMOPC, ~9% DMPS) containing different mole fractions ($\chi$) of Texas Red-DPPE ligand (N-(Texas red sulfonyl)-1,2-dihexadecanoyl-sn-glycero-3-phosphoethanolamine), after incubation with 20 μg/ml anti-Texas Red rabbit monoclonal IgG antibody. FIG. 4b is a plot of g(r) for a series of identical dispersions of 6.8 μm diameter particles ($\phi$=0.25) derivatized with membranes containing the ganglioside $G_{TTB}$ (trisialoganglioside), which have been incubated with various concentrations of tetanus toxin (TT). Binding of TT to membrane surface $G_{TTB}$ induces a condensed to dispersed phase transition as detected in the g(r) plots as well as by direct observation of the colloid (inset images). FIG. 4c is a plot showing the results of a series of experiments as in FIG. 4b, except with 0.5% monosialoganglioside ($G_{M1}$) in place of $G_{TTB}$. Binding of Cholera Toxin B-subunit (CTB) to the $G_{M1}$ membrane surface induces the transition. Incubation of CTB with $G_{TTB}$ colloids or TT with $G_{M1}$ colloids produced no effect.

DETAILED DESCRIPTION

Figure 1:
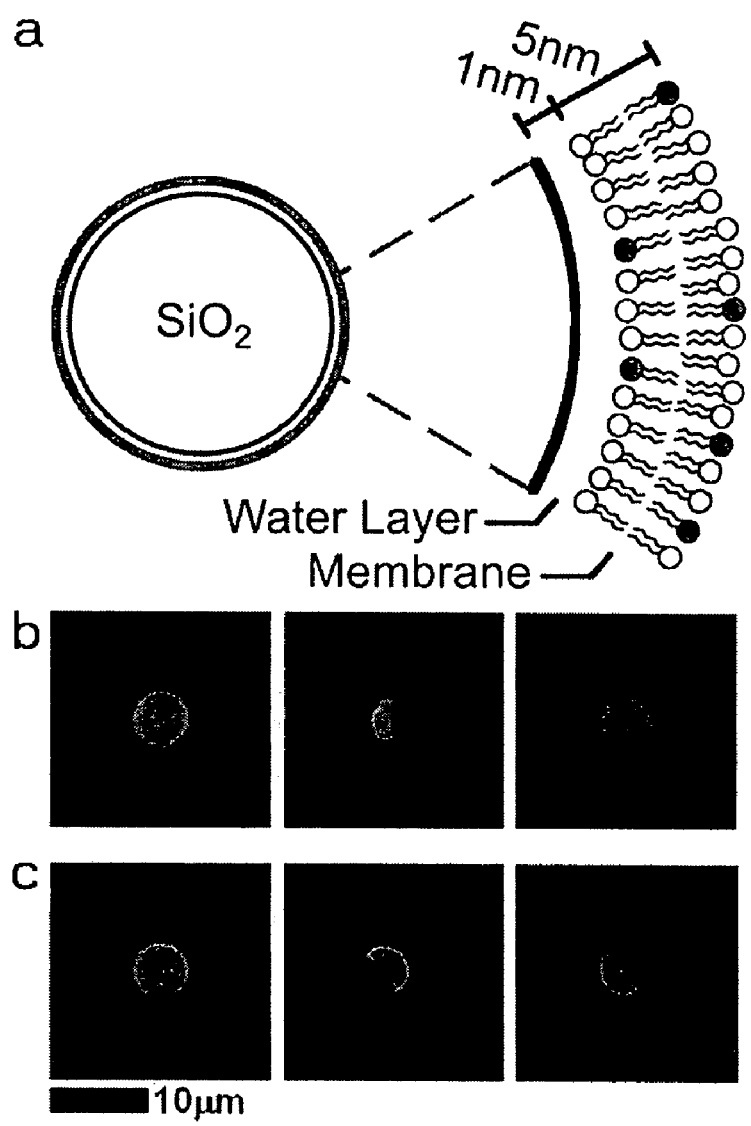
FIG. 1a is a schematic diagram of a membrane-derivatized silica particle.
FIG. 1b shows three photographs detailing fluorescence recovery after photobleaching (FRAP) experiments conducted on the lipid membrane coating the particle's surface for fluid membranes. The photographs show full illumination prior to bleach (left), exposure pattern during bleach (middle), and full illumination 1 min. after bleach (right).
FIG. 1c shows the same fluorescence recovery, but with a non-fluid membrane.

Embodiments of the invention relate to an assay for detecting binding between a ligand and an analyte. In the assay, as discussed below, a population of colloids is first associated with a ligand to create a population of modified colloids. The modified colloids are then incubated together under conditions wherein they are near, or at, a phase transition state. Under such conditions, the modified colloids are mostly in a condensed phase, but nearing transition to a dispersed phase. Relatively minor perturbations of the colloidal mixture conditions can lead the modified colloids to transition into a mostly dispersed phase.

It was discovered that the addition of an analyte which binds to the associated ligand can result in a phase transition of the modified colloids from a mostly condensed phase to a mostly dispersed phase. Using this discovery, it was possible to develop a sensitive assay to detect binding of any analyte to a ligand by determining the phase of the population of modified colloids following analyte treatment.

It should be noted the embodiments of the invention are not limited to phase transitions from condensed to dispersed phases. In fact, binding of an analyte to a ligand could be detected by measuring a phase transition from a dispersed to a condensed phase.

The behavior of a colloidal system is driven by the pair interaction potential between particles. In the case of membrane-derivatized silica particles, the pair potential is dominated by membrane-membrane interactions. Two-dimensional dispersions of lipid membrane-derivatized silica particles exhibit colloidal phase transitions that are governed by details of these membrane surface interactions. The collective phase behavior serves as a cooperative amplifier that produces a readily detectable response from a small number of molecular events on the membrane surface.

It should be realized that such assays do not require the use of a labeling technique to tag the colloid, the analyte, or the ligand. Phase transitions of the microspheres can be detected optically, such as with a microscope. Accordingly, embodiments of the invention provide an advantage in that it is not necessary to stain or label any of the components in order to detect analyte-ligand binding events.

However, it should be realized that the assay is not limited to non-labeled constituents. Under some circumstances, it may be advantageous to label the colloids, the ligand or the analyte. For example, in one embodiment, a heterogeneous mixture of microspheres are labeled, and their dispersion pattern thereafter detected by measuring the position of the label following treatment with the analyte. In another embodiment, the heterogeneity of the colloidal particles may be discernable due to substantial differences in the size of individual particles.

In addition, the phase transitions are preferably dynamical phase transitions. As used herein a dynamical phase transition is one wherein virtually the entire population moves from one phase to another. In addition, the constituent parts of the population may also be dynamically moving. For example, a dynamical phase transition of a colloid population is one in which the phase of virtually the entire colloidal population changes, for example, from a condensed phase to a dispersed phase. However, colloidal particles within the population also dynamically associate with a variety of other colloidal particles. From a macroscopic view, the colloid population may or may not move from one phase to another. The freedom of the colloid to change phase, however, does exist. At the particle level, however, each particular colloidal particle pairs and un-pairs an arbitrary number of times with an arbitrary number of other particles. Thus the particles are never irreversibly associated with each other. This is in contrast to detection methods such as agglutination, for example, which are not representative of a dynamical phase transition. This is because the constituent parts of an agglutinate do not dynamically interact with one another following a transition state; In an agglutination, the constituents remain bound to one another in a fixed configuration.

As discussed below, embodiments of the invention also include a method of detecting the presence of an analyte using statistical analysis of the collective behavior of a population of particles after contact by the analyte. Using direct optical imaging, multiple near-equilibrium phases were observed, and it was discovered that analyte binding to a particle surface at densities as low as $10^{-4}$ monolayer can trigger a phase transition. Statistical analysis enables quantitative comparison among different systems and reveals subtle, pre-transition effects and signature post-transition behavior. In some embodiments, particle distribution is measured by calculating particle pair distribution functions, but other analyses may be used, including, but not limited to, higher-order correlation functions. The binding event on the surface of a particle which achieves a phase transition at or near equilibrium was found to produce a recognizable signature effect on the random distribution of the particle that could be interpreted and calculated by statistical analysis, as discussed in more detail below.

The following abbreviations are used throughout the specification and drawings:
FRAP—fluorescence recovery after photobleaching;
g(r)—pair distribution function;
DMOPC—1,2-Dimyristoleoyl-sn-glycero-3-phosphocholine;
DMPS—1,2-dimyristoyl-sn-glycero-3-[phospho-L-serine];
DOEPC—1,2-dioleoyl-sn-glycero-3-ethylphosphocholine;
NBD-PE—1,2-Dioleoyl-sn-Glycero-3-Phosphoethanolamine-N-(7-nitro-2-1,3-benzoxadiazol-4-yl;
Texas Red-DPPE—N-(Texas red sulfonyl)-1,2-dihexadecanoyl-sn-glycero-3-phosphoethanolamine;
$G_{T1B}$—trisialoganglioside;
$G_{M1}$—monosialoganglioside;
TT—tetanus toxin;
CTB—Cholera Toxin B-subunit; and
BT—α-Bungarotoxin Particle Compositions As is known, colloidal particles can self-assemble into a variety of ordered phases. The collective behavior of colloidal particles is largely determined by the pair interaction potential between particles, which are in turn governed by the surface chemistry of the particles. The characteristics of the colloidal particles are thus important in determining the sensitivity and other aspects of the assay.

The terms "colloid" and "colloidal particle" are used interchangeably herein, and are defined to mean microscopic particles small enough to exhibit collective behavior in solution. The colloidal particles may have a diameter of about 10 nm to 50 μm, and are preferably about 1 μm-6.8 μm in diameter, and more preferably about 5 μm-6.8 μm. The particles may be of any shape, but are preferably essentially spherical. In one embodiment, the colloidal particles are microspheres.

In some embodiments, colloidal particles are inert, such that the bare particles do not significantly interact with one another under the conditions of the assay. In other embodiments, the bare particles may exert attractive or repulsive forces relative to each other. Particles can also be comprised of various materials, including porous and non-porous forms of such materials as silica and silica-containing compounds, polymers such as polystyrene, polymethacrylates, polyacrylates, diacetylenes, alkenes, thiophenes, polythiophenes, glycopolythiophenes, imides, acrylamides, acrylates, methacrylamides, methacrylates, vinylether, malic anhydride, urethanes, allylamines, siloxanes, anilines, pyrroles, and vinylpyridinium and other hydrogel polymeric materials, microgels and hydrogels, gold or other metals, Group II-VI materials, Group III-V materials, branched and unbranched compositions (e.g. demdrimer), other inorganic and organic metals and materials acetylenes.

Colloidal particles may be derivatized with a wide variety of substances, providing a precise method of adjusting the chemical and biological constitution of their surface, and thereby adjusting their behavior in solution. In one embodiment, particles are coated with a lipid layer. The lipid layer can be a bilayer, a monolayer or other structure. The chemical composition of the lipid membrane can be adjusted to modulate the pair interaction potential, and thereby modulate the point at which the particles are at a phase transition state. As used herein, the term "phase transition state" is meant to define that state of a colloidal particle suspension wherein the colloids are about to change from a dispersed phase to a condensed phase, or vice versa. The actual "phase transition" is meant to define the transformation of the colloidal suspension from one phase to another.

In various embodiments, the lipid coated particles enter a condensed phase when the lipid layer has a net neutral or net negative charge. Similarly, in other embodiments the lipid coated particles enter a dispersed phase when the lipid layer has a net positive charge. In a preferred embodiment, the lipid layer is comprised of a mixture of neutral and negatively charged lipids, with about 10% of the lipids being negatively charged. However, the assay can be carried out with particles with any surface charge composition.

Lipid membranes can be assembled on silica particles by essentially the same vesicle fusion process used to form supported membranes on monolithic substrates (Bayerl et al., Biophys. J., 58: 357-362 (1990); Buranda et al., Langmuir, 19: 1654-1663 (2003)). Any other suitable method can be used as well, such as those described by Tanaka et al., J. Am. Chem. Soc., 126; 3257-3260 (2004). The lipid layer can be reconstituted from purified components to form a membrane on the particles, or membranes stripped from live cells may be used. The lipid layer is preferably continuous and preferably retains lateral fluidity. In one embodiment, the lipid layer has a diffusion coefficient of about 1-5 $\mu m^2/s$.

FIG. 1a is a schematic diagram of membrane-derivatized silica particle. As shown, the silica ($SiO_2$) particle is associated with a water layer of approximately 1 nm and a lipid bilayer that is approximately 5 nm in width. FIG. 1b shows three photographs detailing fluorescence recovery after photobleaching (FRAP) experiments conducted on the lipid membrane coating the particle's surface for fluid membranes. The photographs show full illumination prior to bleach (left), exposure pattern during bleach (middle), and full illumination 1 min. after bleach (right). FIG. 1c shows the same fluorescence recovery, but with a non-fluid membrane.

The lipid layer can generally include any component of biological or synthetic membranes, including, but not limited to, lipids, cholesterols, steroids, ergosterols, polyethylene glycols, proteins, peptides, or any other molecules such as fatty acids, triacylglycerols, glycerophospholipids, sphingolipids (e.g. sphingomyelins, cerebrosides and gangliosides), sterols, cholesterol, surfactants, polysorbate, octoxynol, sodium dodecyl sulfate, zwitterionic detergents, decylglucoside, deoxycholate, diacetylene derivatives, phosphatidylserine, phosphotidylinositol, phosphatidylethanolamine, phosphatidylcholine, phosphatidylglycerol, phosphatidic acid, phosphatidylmethanol, cardiolipin, ceramide, lysophosphatidylcholine, D-erythrosphingosine, sphingomyelin, dodecyl phosphocholine, N-biotinyl phosphatidylethanolamine, and other synthetic or natural components of cell membranes that can be associated with a membrane or membrane assemblies such as liposomes and films.

In one embodiment, the membrane is comprised of a neutral and a negatively- or positively-charged lipid monomer, more preferably a neutral and a negatively-charged lipid. Suitable lipids can include, but are not limited to, phosphatidylserine, dipalmitoylphosphatidic acid, 1,2-Dimyristoleoyl-sn-glycero-3-phosphocholine (DMOPC), 1,2-dimyristoyl-sn-glycero-3-[phospho-L-serine] (sodium salt) (DMPS), and 1,2-dioleoyl-sn-glycero-3-ethylphosphocholine (DOEPC), distearoylphosphatidylglycerol, phosphatidylinositol, 1,2-dioleoyl-3-dimethylammonium-propane, 1,2-dioleoyl-3-trimethylammonium-propane, dimethyldioctadecylammonium bromide, 1,2-dioleoyl-sn-glycero-3-ethylphosphocholine, N-(7-nitrobenz-2-oxa-1,3-diazol-4-yl)-1,2-dihexadecanoyl-sn-glycero-3-phosphoethanolamine ammonium salt, and N-1,2-dihexadecanoyl-sn-glycero-3-phosphoethanolamine triethylammonium salt, L-a-Phosphatidylcholine (Egg PC), Cholesterol, N-Dinitrophenylaminocaproyl Phosphatidylethanolamine (DNP-Cap PE), ceramides (natural and synthetic preparations), N-[12-[(7-nitro-2-1,3-benzoxadiazol-4-yl)amino]dodecanoyl]-Sphingosine-1-Phosphocholine (C12-NBD Sphingomyelin), 1,2-Dioleoyl-sn-Glycero-3-Phosphoethanolamine-N-(Cap Biotinyl), 1-Palmitoyl(D31)-2-Oleoyl-sn-Glycero-3-Phosphoinositol (and other Phosphoinositol extracts), and polyethylene glycols of various lengths.

In a preferred embodiment, the colloidal particles are silica particles derivatized with a lipid membrane comprising 1,2-Dimyristoleoyl-sn-glycero-3-phosphocholine (DMOPC), 1,2-dimyristoyl-sn-glycero-3-[phospho-L-serine] (sodium salt) (DMPS), and 1,2-dioleoyl-sn-glycero-3-ethylphosphocholine (DOEPC), and the membrane is doped with a ligand specific for an analyte. Upon binding an analyte, a disruption of the polymer backbone occurs, resulting in a detectable phase transition from a condensed phase to a dispersed phase.

In alternative embodiments, the particles may be derivatized with, or completely composed of, non-lipid polymers, such as those disclosed in Discher et al., Science 297:967-973 (2002), or any other material sufficient to achieve the desired pair interaction potentials.

Figure 2:
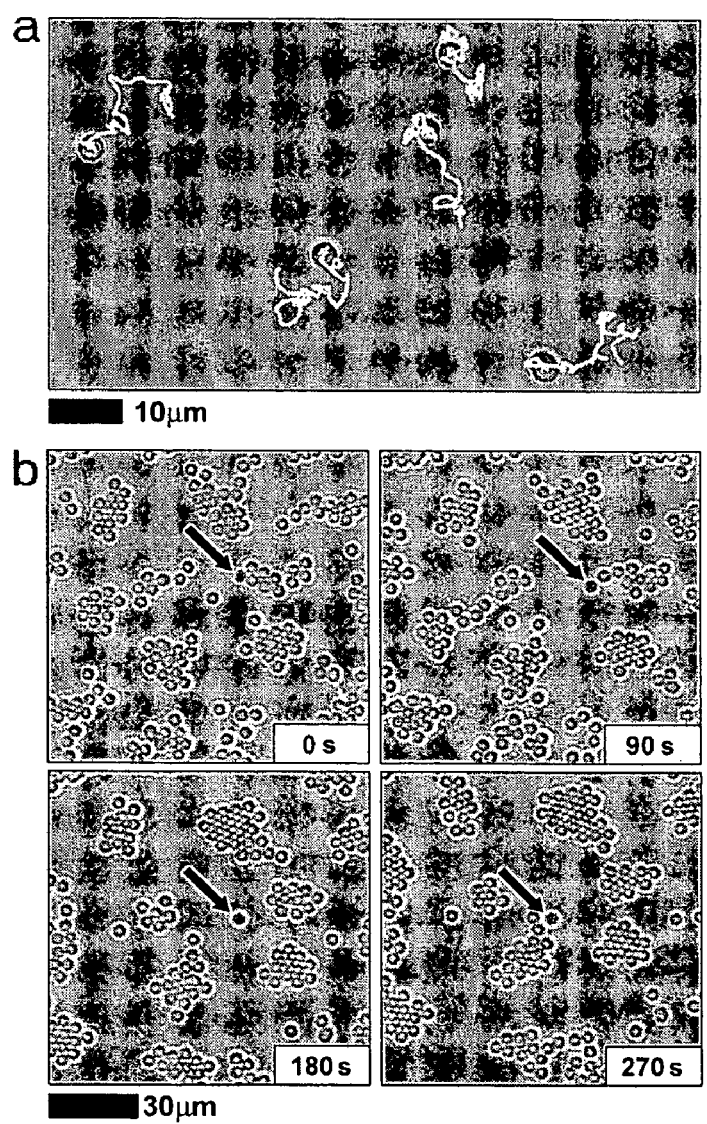
FIG. 2 illustrates the mobility of membrane-derivatized particles.

Particles in suspension were found to exhibit free lateral diffusion and the system behaved as an ergodic fluid. Brownian trajectories for a dilute collection of particles are illustrated in FIG. 2a. Particle diffusion coefficients were essentially independent of membrane composition; measurements ranged from 0.079 to 0.086 $\mu m^2/s$ for 5 $\mu m$ diameter particles.

These values are ~80% that predicted by the Stokes-Einstein relation for purely viscous drag, indicating a small contribution from drag on the underlying substrate. Depending on the strength of the interaction between membranes on the particle surfaces, dispersed (gas) or condensed (liquid or crystalline) phases of the colloid were observed. Particle mobility was retained in condensed phases, with particles found to be not irreversibly associated (FIG. 2b). The mobility of individual particles, in both condensed and dispersed phases, defined the rate of system equilibration. The timescale of particle condensation onto and evaporation from the condensed crystallites, seen in FIG. 2b, was rapid compared to that of our experiments (several minutes vs. more than half an hour). Additionally, the overall morphology and quantitative pair distribution functions of the phases remained constant, despite the interchange of individual particles. These observations suggest that the system is near equilibrium, at least over length-scales of several particle diameters.

The chemical composition of the lipid membrane was adjusted to modulate the pair interaction potential and is described below. Condensed phases, as seen in FIG. 2b, formed whenever the coating membrane was net neutral or negatively charged. In contrast, net positively charged membranes led to dispersed phases. The occurrence of multiple phases indicated that pair interaction energies poise the system near a phase transition. As such, small perturbations on the membrane surface induced significant changes in the macroscopic organization of the colloid.

Ligands

Ligands, as used herein, include ions, molecules, or molecular groups that bind to other chemical entities to form larger complexes. Ligands can include a wide variety of materials, including those described below as potential analytes. Preferably the ligand has a specific affinity for the analyte being detected. Appropriate ligands include, but are not limited to, carbohydrates, nucleic acids, biotin, streptavidin, cytokines, peptides, proteins, lipoproteins, glycoproteins, enzymes, receptors, channels, antibodies, small molecule drugs, larger polymeric drugs, chromophores, antigens, chelating compounds, phosphate and reactive groups, molecular recognition complexes, ionic groups, polymerizable groups, dinitrophenols, linker groups, electron donor or acceptor groups, hydrophobic groups, hydrophilic groups, organic or inorganic molecules, or any molecule that binds to receptors. Additionally, multiple ligands can be associated with a single colloid. The broad range of ligands that may be utilized allows for detection and characterization of binding with a diverse group of analytes.

Ligands may be associated directly or indirectly to the surface of the colloidal particles. As used herein, two molecules are "associated" when they are bound to one another in any manner. For examples, two molecules are associated if they are non-covalently linked. In another embodiment, two molecules are associated if they are covalently linked. In some embodiments, ligands are interspersed in a lipid layer on the outer surface of a colloidal particle. This type of doping of lipid membranes has been described by Salafsky et al., Biochemistry, 35: 14773-14781 (1996), and Groves at al., *Biophys. J.,* 71: 2716-2723 (1996), both of which are hereby incorporated by reference in their entirety. In some embodiments, ligands are incorporated directly into the membrane, while in others they are bound indirectly to the membrane, for example via a glycosyl phosphatidylinositol (GPI) linker incorporated into the membrane, while still in others, are naturally present in the membrane, as is the case with native membrane extracts. The ligands may be inserted into the lipid layer at concentrations of about $10^{-2}$ to $10^{-6}$ molar, more specifically at concentrations of about $10^{-2}$ to $10^{-4}$ molar, or may be present in typical in-vivo concentrations in native lipid membranes. In other embodiments, ligands are covalently coupled directly to the surface of the particle. For example, ligands such as antibodies or antibody binding fragments may be coupled directly to silica, styrene, magnetic, or semiconductor nanocrystal particles. Non-limiting examples of antibody fragments include Fab fragments, Fab2 fragments and single chain antibodies.

Analytes

As used herein, an analyte is any substance or chemical constituent that is undergoing analysis. The analyte can be comprised of an unlimited variety of substances that preferably bind to the ligand. Examples of analytes include toxins, hormones, enzymes, lectins, proteins, signaling molecules, inorganic or organic molecules, contaminants, antibodies, viruses, bacteria or other pathogenic organisms, or idiotopes or other cell surface markers.

In some embodiments, the analyte may comprise a variety of substances whose presence is indicative of a pathogenic organism, including, but not limited to, sialic acid to detect HIV, *Chlamydia, Neisseria meningitidis, Streptococcus suis, Salmonella,* mumps, newcastle, and various viruses, including reovirus, Sendai virus, and myxovirus; 9-OAC sialic acid to detect coronavirus, encephalomyelitis virus, and rotavirus; non-sialic acid glycoproteins to detect cytomegalovirus and measles virus; peptide sequences to hybridize to and identify the presence of Anthrax, CD4, vasoactive intestinal peptide, and peptide T to detect HIV; epidermal growth factor to detect vaccinia; acetylcholine receptor to detect rabies; CD3 complement receptor to detect Epstein-Barr virus; β-adrenergic receptor to detect reovirus; ICAM-1, N-CAM, and myelin-associated glycoprotein MAb to detect rhinovirus; polio virus receptor to detect polio virus; fibroblast growth factor receptor to detect herpes virus; oligomannose to detect *Escherichia coli*; ganglioside $G_{M1}$ to detect *Neisseria meningitidis*; and antibodies to detect a broad variety of pathogens (e.g., *Neisseria gonorrhoeae, V. vulnificus, V. parahaemolyticus, V. cholerae,* and *V. alginolyticus*).

The analyte may also comprise any of the substances described above as potential ligands.

Detection Assay

The detection assay is used to determine whether the analyte has bound to the ligand. In some embodiments, the assay comprises the steps of: adding particles bearing a ligand of interest to a solution to form a colloidal suspension. The particles are then allowed to achieve an equilibrium or near equilibrium distribution so that the particles are at or near a phase transition state. The distribution of the particles relative to one another is then measured at that phase so that it can be compared to the particle distribution following addition of the analyte. The analyte is then added to the colloidal suspension and the colloidal particles are allowed to re-establish an equilibrium or near equilibrium distribution. The particles relative distribution to one another is then measured again to determine if the analyte has bound to the ligand. If the distribution of particles indicates that they have transitioned from one phase to another, for example from a mostly condensed phase to a mostly dispersed phase, then it is determined that the analyte has bound to the ligand.

In other embodiments, the assay comprises the steps of: adding colloidal particles bearing a ligand of interest to a solution to form a colloid; allowing the colloidal particles to achieve an equilibrium or near equilibrium distribution; detecting the distribution of the particles relative to one another; isolating the colloidal particles; adding the isolated particles to a second solution potentially containing an analyte that binds the ligand; allowing the colloidal particles to re-establish an equilibrium or near equilibrium distribution; and detecting the distribution of the particles relative to one another to determine if the analyte is present in the sample.

Additional embodiments of the assay can include the steps of: adding colloidal particles bearing a ligand of interest to a solution to form a colloid; allowing the colloidal particles to achieve [dynamic] an equilibrium or near equilibrium distribution; detecting the distribution of the particles relative to one another; isolating the colloidal particles; adding the isolated colloidal particles to an environment potentially containing an analyte that binds the ligand; isolating the colloidal particles from the environment; adding the colloidal particles to a solution; allowing the colloidal particles to re-establish an equilibrium or near equilibrium distribution; and detecting the distribution of the particles relative to one another to determine if the analyte is present in the sample. The collective phase behavior serves as a cooperative amplifier that produces a readily detectable response from a small number of molecular events on the membrane surface.

In one embodiment, analyte binding is detected by observing a transition from a condensed to a dispersed phase. To achieve a condensed to dispersed phase transition upon binding, the assay conditions, such as the size and surface composition of the particles and composition of the assay solution, are such that the particles form a condensed phase in the absence of the analyte due to attractive forces among the particles (e.g., van der Waals interactions). If an analyte added to the solution binds to a particle-associated ligand, its interaction with the particle surface can increase the closest approach position between two particles and, correspondingly, reduces the cumulative strength of the attractions between them (see, Wong and Groves, *Proc. Natl. Acad. Sci. USA*, 99: 14147 (2002)). In this way, the binding of the analyte can affect the aggregation, distribution and behavior of the colloidal particles in a manner that allows detection of binding by measuring the distribution of the particles. Statistical analysis of particle pair distribution functions enable quantitative comparison among different systems and can reveal subtle analyte-ligand interactions. In addition, binding events can produce recognizable signature effects on the random distribution of the particles that can be correlated with particular interactions.

It should also be realized that detection of the analyte is not a binary event. For example, the strength or weakness of binding to the ligand can be accurately measured by the present assay (see, FIGS. 8A-8C). By determining the extent to which the colloidal particles have transitioned from a condensed to a dispersed state, one can estimate the amount of binding between the analyte and the ligand. A larger number of colloids that transition from a condensed to a dispersed state is indicative of a stronger ligand binding, whereas a fewer number of colloids transitioning from a condensed to a dispersed state indicates that the ligand bound more weakly to the analyte.

Figure 8A:
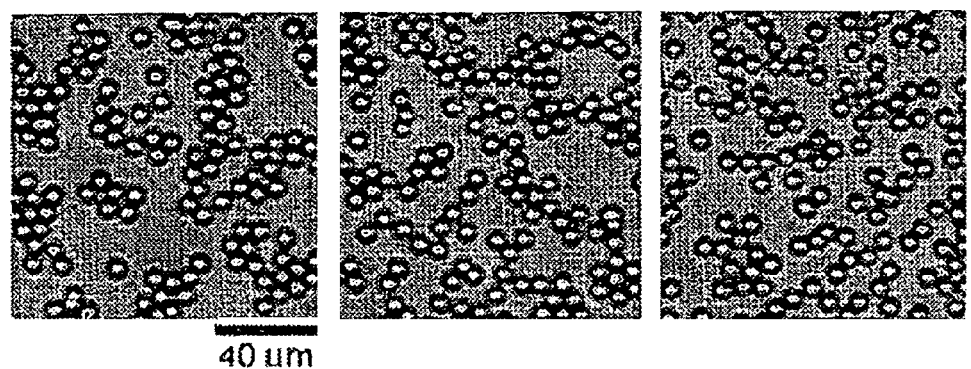
FIG. 8a is a photograph of three images depicting varying states of aggregation of membrane-coated silica microbeads upon binding of CTB to membrane-associated $G_{M1}$ with 1 nM (left), 50 nM (middle), and 1000 nM (right) CTB incubations.
Figure 8B:
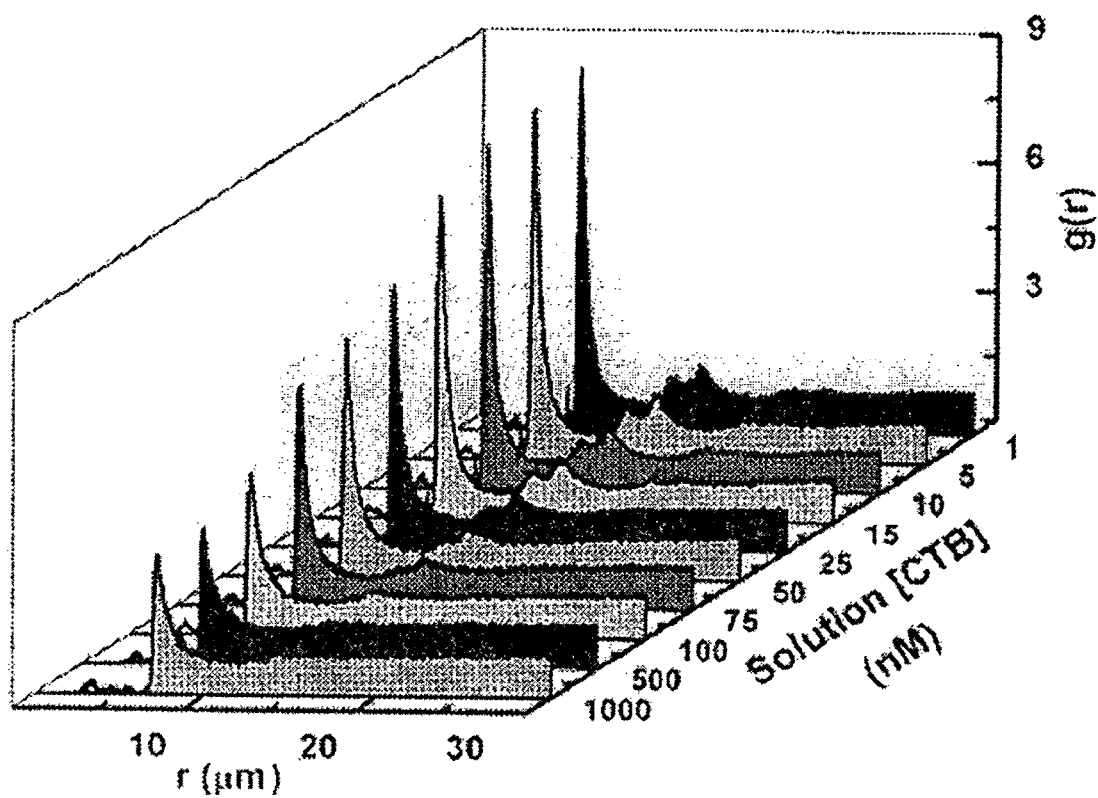
FIG. 8b is a graph showing a series of plots of radial distribution functions for 0.5 mol % $G_{M1}$ membrane-coated beads incubated with increasing concentrations of CTB.
Figure 8C:
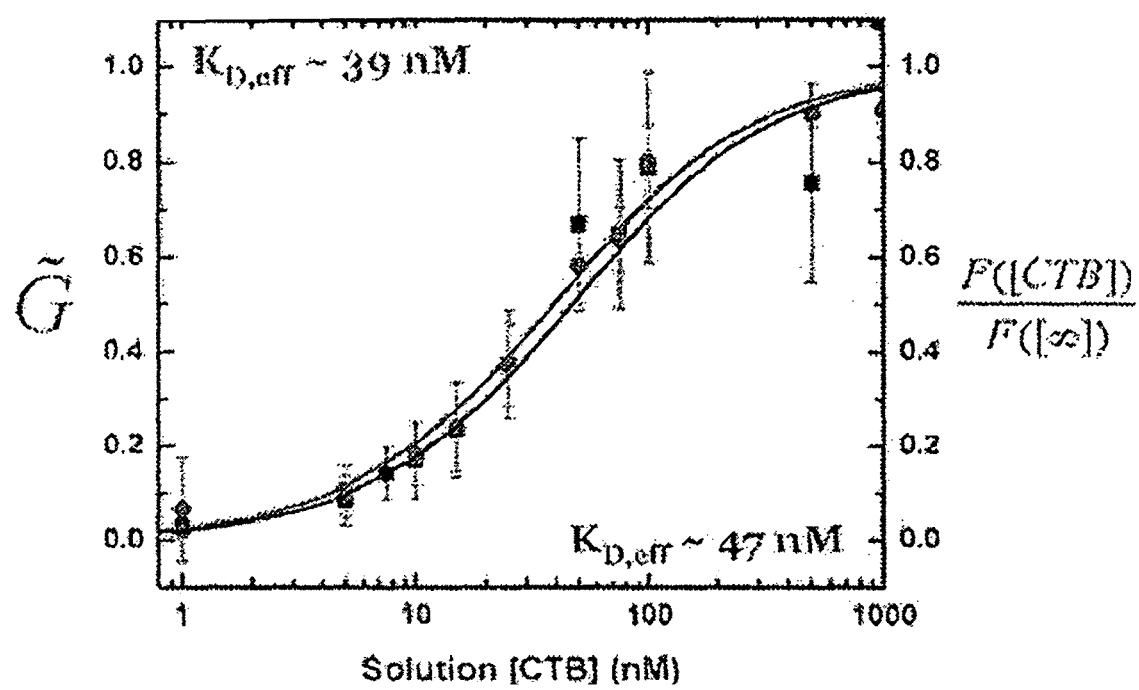
FIG. 8c is a line graph illustrating a comparison between equilibrium binding curves obtained from a colloid assay (dashed) and conventional fluorescent read-out (solid).
Figure 9:
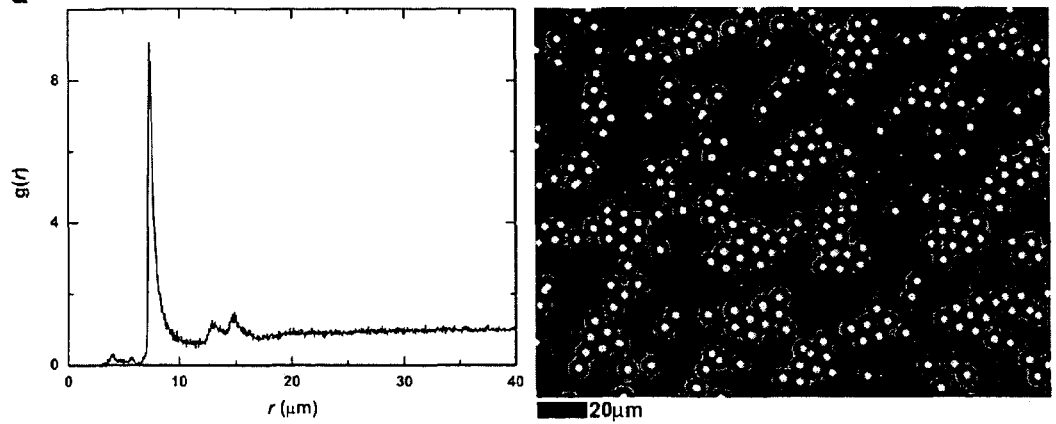
FIG. 9a is a plot of measured g(r) for a dispersion of 6.8 μm mean-diameter beads (area fraction ($\phi$=0.15) derivatized with human erythrocyte membrane (left). Corresponding image depicts a representative distribution (right).
FIG. 9b is a plot of measured g(r) for a dispersion of 6.8 μm mean-diameter beads (area fraction $\phi$=0.15), derivatized with human erythrocyte membrane and incubated with an excess of anti-Band III mouse monoclonal antibody (left). Corresponding image depicts a representative distribution (right).
Figure 9:
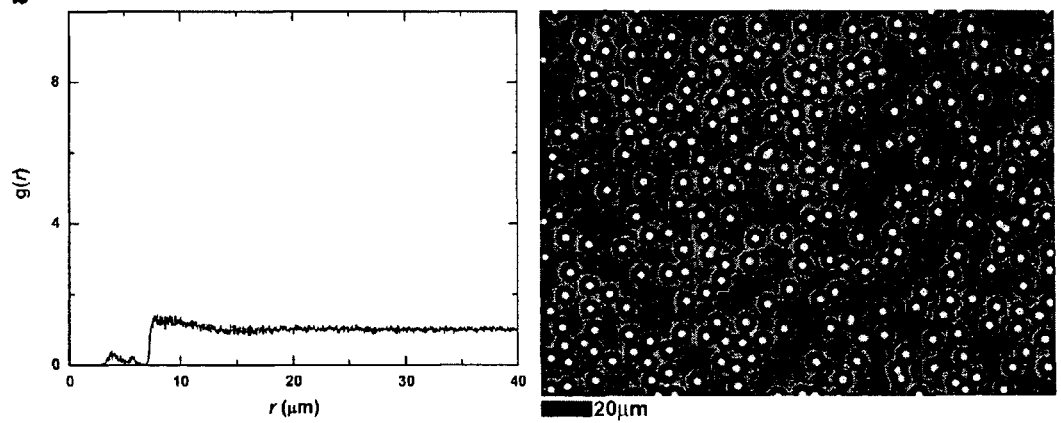

FIGS. 8A-8C illustrate the measurement of binding affinities using membrane-derivatized colloids. Binding of CTB to membrane-coated silica microbeads with membrane-associated $G_{M1}$ was measured at a range of CTB concentrations. A plot of the radial distribution functions allowed for the quantitative comparison of colloidal distributions over the range of protein concentrations used. A comparison between the equilibrium binding curves obtained from colloid assay and binding curves obtained using conventional fluorescence methods revealed that the colloid pair distribution function results from the colloid assay scale with the bound protein concentrations measured via fluorescence. Thus, the colloid assay provides a label-free assay of binding affinity, that can be used to accurately determine the equilibrium dissociation constants for a wide variety of interactions.

In one embodiment, the attractive forces among the particles poise the system close to a phase transition in the absence of the analyte. In some embodiments, the assay can be calibrated to confirm that the system is near a phase transition threshold by observing a phase transition in response to varying of the ionic strength of the assay solution, the temperature, or other variables which affect the affinity of particle-particle attractions. The assay is generally more sensitive when the system is near the threshold of a phase transition state, allowing small perturbations in binding between ligands and analytes to trigger a readily detectable phase transition. However, some embodiments of the invention detect binding without the population of particles being at or near a phase transition, either in the presence or absence of the analyte.

Figure 7A:
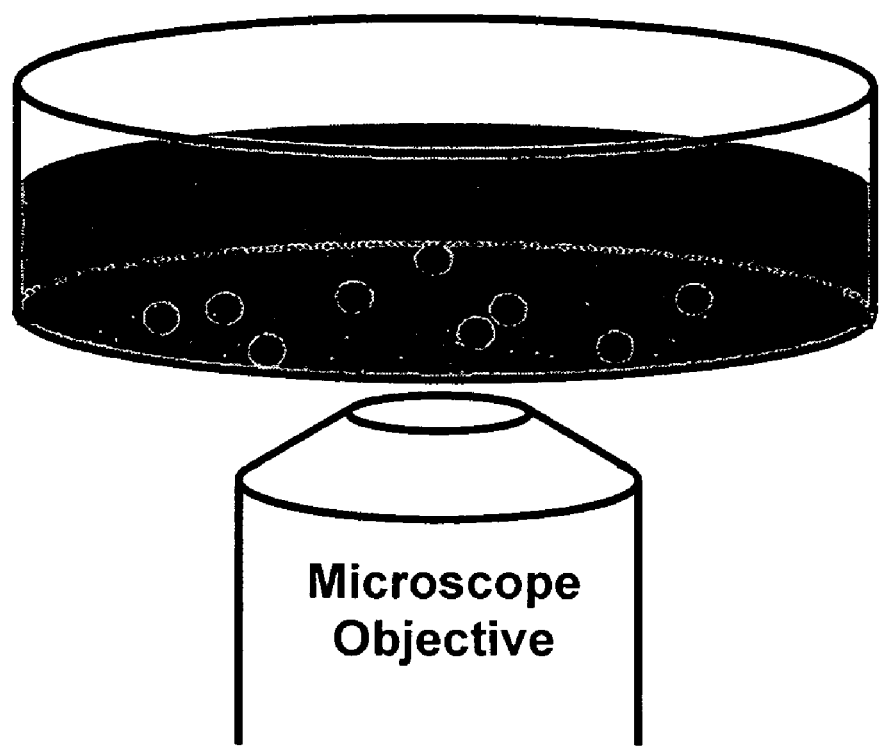
FIG. 7a is a schematic illustration showing derivatized colloidal particles observed by direct optical imaging.

In order to view the particles, they typically settle due to gravity in the equilibrium or near equilibrium state. The particles can settle on a substantially planar surface to form a "two-dimensional colloid", which is a layer of colloidal particles normally on the surface of a substrate (FIG. 7*a*). The two-dimensional colloid facilitates viewing and imaging of the particles, and statistical analysis of their distribution on the surface. The colloidal particles are preferably used in concentrations that yield, when the particles are arrayed on the bottom of a well or plate, a fraction of about 0.1 to 0.5, or more preferably 0.15-0.25, of the area occupied by particles as opposed to spaces between or around the particles. More particles tend to make the assay more sensitive. Particle mobility is retained in the equilibrium and near-equilibrium phases, and degree of particle mobility defines the rate of system equilibration. The time-scale of equilibration in some embodiments is less than several minutes. In other embodiments it is less than about 30 minutes.

The assay typically requires no application of external force, but rather relies on the thermodynamic behavior of the population of colloidal particles. The colloidal solution preferably exhibits the characteristics of an ergodic fluid when the system is at or near equilibrium, both in the presence or absence of the analyte. Single particles migrate over time into a cluster, into a stand alone position, and back into a cluster. The colloidal particles are free to move about and change relative positions within the suspension. This property allows for the detection of dynamic, reversible, and/or 'weak' binding interactions, since the assay does not require the formation of static complexes. This is in contrast to existing techniques, such as co-precipitation, affinity chromatography, and the like which require the formation of stable complexes to detect binding. Individual particle mobility is unaffected by protein binding, so exposure to a particular analyte of interest triggers a phase transition when the appropriate cognate ligand has been incorporated into the colloid membrane.

Alternative embodiments can utilize heterogeneous mixtures of particles to examine complex interactions. Particles can be labeled so they are individually identifiable. Such labels include, but are not limited to, fluorescent molecule doped into a particle material, fluorescent molecules doped into a lipid layer, semiconductor nanocrystals doped into particle material, and the like. Particles can also be distinguished according to size. For example, some embodiments utilize heterogeneously sized particles, with each particle having distinct properties, for example through modification of the particle surface or materials, or through particle size itself (e.g., varying surface areas available for interactions). A wide range of particle sizes may be used in the assay. In one embodiment, particles of about 3-7 μm diameter are used, and variations in diameter of ~50% give detectable differences in phase behavior. In this embodiment, detectable differences in particle sizes provides a means for identifying and tracking the behavior of particular particles. In various embodiments, tracking the behavior of particles with particular properties allows detection of complex inter-molecular interactions. For example, strongly interacting particles of heterogeneous composition and functionality can be used as building blocks for assembly into complex, multi-functional, nanoscale structures that can be used in the analysis of more complicated systems. Colloidal particles can also be functionalized internally with materials such as fluorescent labels, semiconductor nanocrystals, nano-scale detection devices, or custom-designed nanocrystals or molecules.

In other embodiments, particles can be mixed with live cells. In these embodiments, a cell surface protein or other molecule serves as the analyte, which causes a detectable change in the distribution of the particles upon binding of the ligand. This allows for the detection of cell activation and proliferation events (e.g. cell rosetting), cellular interactions, multiplexing, and other physiologically relevant events.

Colloidal particles can be dispersed into many different environments to detect the presence of an analyte of interest, such as the human body, areas where extreme toxics or caustics are present. The particles can also be used in high vacuum settings. In these embodiments, the binding event is allowed to occur, and the particles are then collected and subjected to conditions which allow the assay to be performed. Since only a finite number of particles having undergone the binding event must be collected, the particles can be dispersed in such environments as a flowing body of water, e.g. a river, or a living organism. In some embodiments, "sensor" particles exposed to the analyte sample can be moved through a plurality of background particles that were not exposed to the analyte sample. This allows the detection step to be performed with a small number of sample-exposed particles by observing the phase behavior of the "sensor" particles in relation to the background particles.

Implementation of the colloid assay is amenable to automated liquid handling and imaging systems to facilitate high throughput analysis. For example, automated fluid handling systems may be employed to perform the steps of the assay in one or more test wells. In a preferred embodiment, the assay is carried out in Corning COSTAR 3997 polystyrene plates, or comparable high throughput plates. Automated fluid handling allows multiple assays to be performed simultaneously under a variety of conditions by achieving uniform and repeatable treatment of samples. The fluid handling device can be programmed to control assay conditions such as temperature and incubation times, to add and remove samples from the test wells, and to perform the detection steps of the assay, among other things. Robotic fluid handling devices are available commercially, for example, from Tecan AG.

In some embodiments, the detection steps of the assay can be carried out by measuring a variable known to correlate with a phase transition, preferably where the variable is easier to measure than the distribution of the colloidal particles. For example, a spectrophotometer, scanning plate reader, or similar device that images or calculates light scattering can be used to measure the optical density of a particle population before and after addition of the analyte, and particular readings can be correlated to the occurrence or non-occurrence of a phase transition. Additional assays can then be carried out in a high throughput manner in which binding of an analyte to the ligand is detected by scanning the plate to determine whether a signature optical density reading is achieved, indicating the occurrence or non-occurrence of a phase transition.

Other aspects of the invention that may be varied include the hydration, coatings, and charge of the materials used in the assay.

Detection

The distribution of the population of particles can be expressed in terms of the pair correlation and the phase transition can be mapped by analyzing the functions. The minimum population number is 2, preferably at least 10, more preferably 1000.

Figure 3:
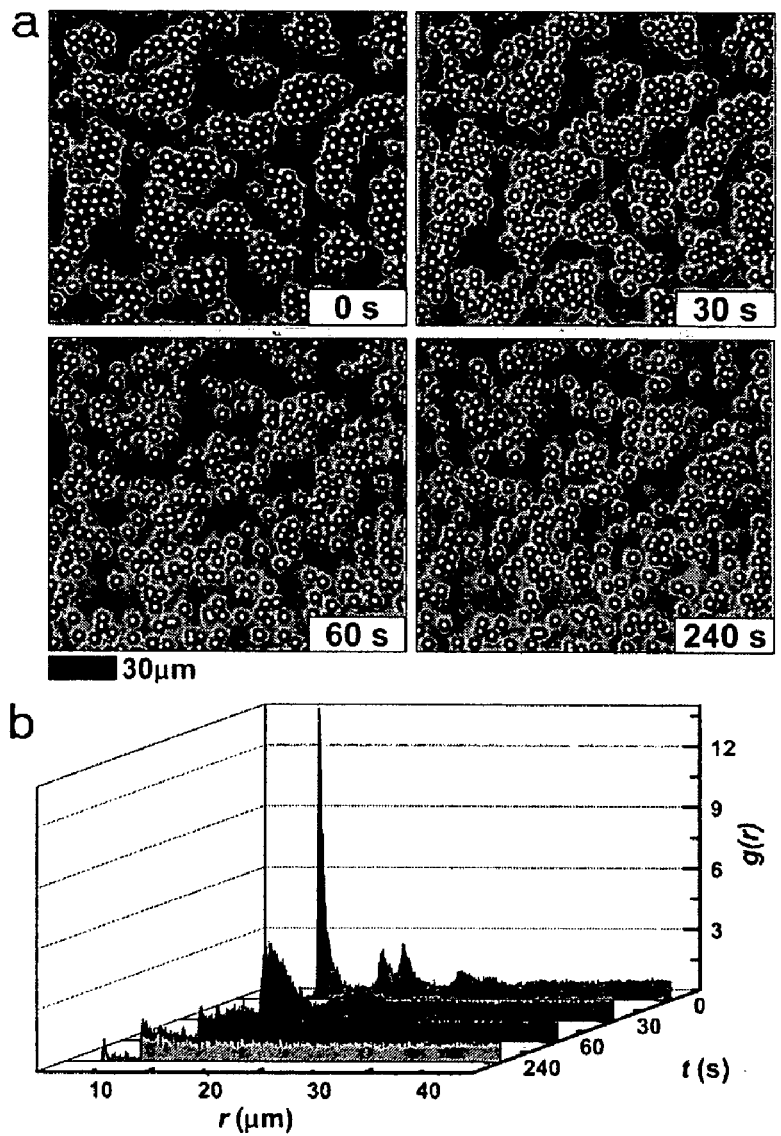
FIG. 3 illustrates a protein binding-triggered colloidal phase transition.

FIG. 3 depicts a time sequence of a phase transition from a condensed phase to a dispersed phase triggered by addition of analyte protein at t=0 s (FIG. 3a top left panel). Within seconds of adding a drop of a solution containing an analyte to the top of the well, uniform disruption of the condensed phase is discernable (FIG. 3a top right panel). At about a minute, the colloid attained a measurable dispersed distribution (FIG. 3a bottom panels). Individual particle mobility was unaffected by protein binding, so exposure to a particular analyte of interest triggered a phase transition only when the appropriate cognate ligand has been incorporated into the colloid membrane. The physical presence of the analyte bound to the membrane surface increases the closest approach position between two membranes and, correspondingly, reduces the cumulative strength of the van der Waals attraction between particles, enabling the phase transition.

Figure 7B:
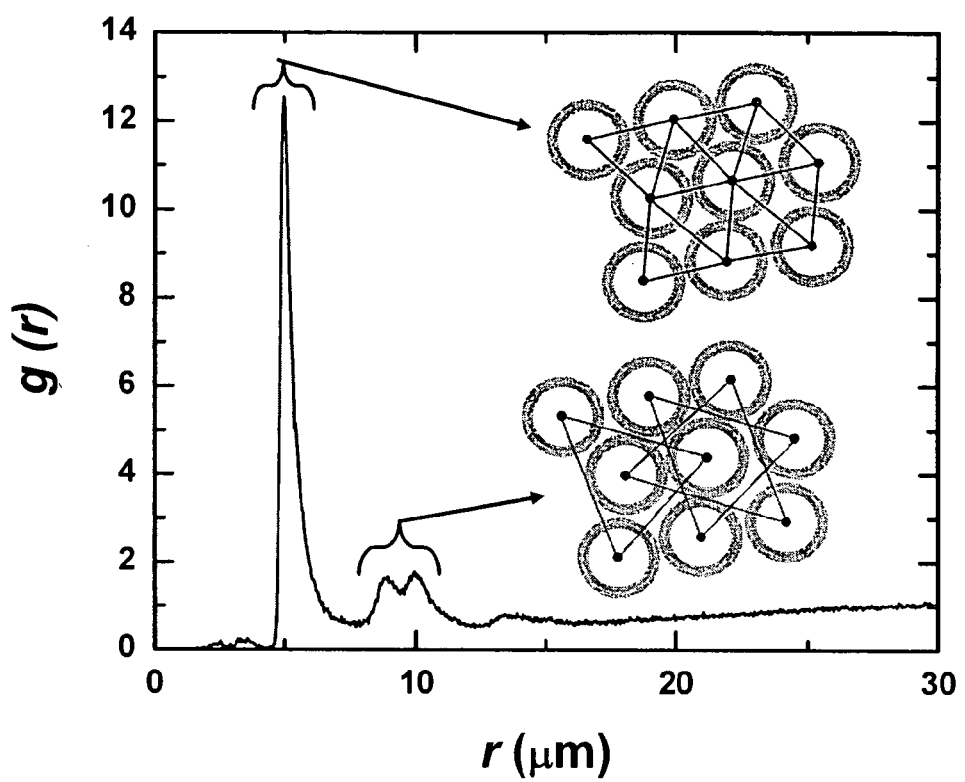
FIG. 7b is visual representation of the nearest-neighbor interactions that correspond to the different peaks in a g(r) plot of homogeneous colloidal particles.

Quantitative analysis of the colloidal phases was performed by extracting the pair distribution function, g(r). Particle positions were measured from wide-field (~1 mm$^2$) images by an object locating algorithm to a precision of ~16 nm. Wide field images of large populations of particles should be taken with a high resolution camera such as a charged-coupled device camera and analyzed with imaging software such as METAMORPH (Universal Imaging Corporation, Cranberry Township, Pa.). Using such software, the centers of particles can be found very accurately using intensity because the particles are spherical clear objects. The X,Y coordinates of the center of each particle are calculated for each image to calculate the distances between the center of each particle and the centers of its nearest neighboring particles, second nearest neighbors and third nearest neighbors, etc (FIG. 7b).

For a finite rectangular window of spatial dimensions X by Y, g(r) can be computed from $$g(r) = \frac{\eta(r) X^2 Y^2}{N(N-1)\delta r[\pi X Y r - 2(X+Y)r^2 + r^3]} \quad \text{(Equation 1)}$$

where $\eta(r)$ is the number of particle pairs with separation distance $r \pm \delta r/2$ ($\delta r = 40$ nm for the data presented here), r is the radius of particles used and N is the total number of particles.

The number of iterations for a g(r) plot for effective analysis depends on N, the number of particle pairs analyzed. If N=1, to calculate g(r) to satisfaction may require a very long course of time in order to gather enough data to show the particular g(r) plot for that particular composition of particles. Therefore it is preferred that N is at least 10, preferably 1000 or more to gather sufficient data in a matter of seconds.

The condensed phase g(r) is characterized in the curve at t=0 by a large peak at the nearest neighbor separation distance of one particle diameter ($r_0$) and secondary peaks occurring at $r=\sqrt{3}r_0$ and $2r_0$, corresponding to next nearest neighbors in the hexagonal crystallites. Independent measurements of g(r) were highly consistent. Standard deviations in the magnitude of the $r_0$ peak determined from separate colloidal preparations were generally less than 5%. Dispersed phases, consisting of random distributions and correspondingly flat g(r) functions, are visibly distinguishable from condensed phases. (See curves at times 30, 60 and 240 s). Quantitative determination of g(r) additionally distinguishes a range of intermediate distributions. While these can be transient, intermediate degrees of order were also observed in near equilibrium distributions, corresponding with differing amounts of protein binding on the membrane surface.

Quantitative analysis of the colloidal phases can further be performed by extracting an infinite series of distributions. This is used when the number of colloidal particle types is greater than 1.

For quantitative comparison among samples, the first peak in g(r) is isolated which occurs at the particle diameter (5 μm). The corresponding effective interaction energy, $E_i$. $E_i$ is then computed as an approximation of the $k_B T$ energy and calculated by taking the natural log of the height of the first peak in the g(r) plot and either fitting it to a curve having a known function or expression, or by integrating the area under the curve. This allows precise comparison among samples containing equal area fractions (φ) of particles and $E_i$ converges to the pure pair interaction energy at low coverage densities. Although equilibrium is required for $E_i$ to have meaningful units of energy, this is not a requirement for effective comparison. As long as each colloidal system is cast in an initially uncorrelated state, non-equilibrium distribution measurements at defined time intervals can also be used for quantitative comparison.

While the calculation of $E_i$ may be useful, it may not be necessary in cases of analyte detection as used herein. The qualitative g(r) plots show a very distinctive missing first peak when the analyte is detected and bound by the particles being analyzed.

At equilibrium, g(r) is physically related to the potential of mean force, w(r):

$$g(r) = e^{-w(r)/k_B T} \quad \text{(Equation 2)}$$

In dilute systems, w(r) is equivalent to the pair interaction potential and thus provides a direct measure of the interaction energy. In more concentrated systems, w(r) includes effects due to neighboring particles. w(r) can be deconvolved to obtain the true pair potential using the Ornstein-Zernike integral equation along with an appropriate truncating approximation, such as the Percus-Yevick equation.

Independent measurements of g(r) should be highly consistent. Standard deviations among E, values determined from separate colloidal preparations from the same starting materials were generally less than 0.1 $k_B T$.

Precise measurement of g(r) provides a means to explore subtleties of the interactions between different membrane compositions. The transition from condensed to dispersed phases was examined as the net electrostatic charge of the membrane is gradually adjusted from negative to positive.

Several forces, including van der Waals, steric-hydration, and electrostatic contribute to the interaction potential between membranes. Forces between lipid membranes supported on molecularly flat mica surfaces have been studied using the surface forces apparatus (SFA). Under conditions resembling those of the colloid experiments, adhesive interaction energies between mica-supported membranes were of order ~$10^{-22}$ J/$nm^2$ at the minimum separation of ~0.5-1 nm. This was in general agreement with predictions of Derjaguin-Landau-Verwey-Overbeek (DLVO) theory, except for the minimum separation distance, which is determined largely by repulsive steric-hydration forces. The DLVO interaction potential between membrane-derivatized particles was calculated using the linearized Derjaguin approximation for electrostatic interactions and the non-retarded van der Waals potential between two spheres with Hamaker constant=7×$10^{-21}$ J. The van der Waals attraction was strong (350 $k_BT$ at 1 nm minimum separation) and was balanced by electrostatic repulsion, which rapidly becomes dominant at surface potentials of magnitude ≧14 mV (1 nm minimum separation). The large overall magnitude of the DLVO interaction suggests it is improbable that a precise balance between van der Waals and electrostatic forces could lead to the consistently weak adhesion observed experimentally.

One explanation of the experimental results may be constructed based on the fact that the colloidal particles of the invention are not molecularly flat. As two particles approach one another, regions of relatively higher surface topography experience shorter interaction distances. Details of the contact geometry between rough surfaces produce differential effects on the various inter-particle forces, based on the characteristic length scales over which they act. For example, surface topography on the nanometer length scale is expected to have little effect on electrostatic interactions due to the long Debye lengths (>100 nm) in these experiments. In contrast, the short-range van der Waals interaction is strongly modulated by nanometer-scale surface topography: most of the adhesive energy will come from the small fractional area of the surfaces in closest contact. The similarly short range steric-hydration forces will determine the minimum separation distance between two particles based on the these close contact regions as well. Large surface areas are thus precluded from experiencing short-range interaction forces due to surface topography.

Analyte binding to the membrane surface creates topography and changes the effective roughness. This suggests a possible mechanism for the analyte binding-induced colloidal phase transition in which the presence of a few proteins on the membrane surface shifts the closest approach position between two particles and, correspondingly, modulates the cumulative strength of the van der Waals attraction. The experimental ability to modulate the interaction energy by adjustments in the membrane composition is of practical importance for the design and optimization of analytical systems based on this type of colloidal phase transition.

The detection assay of the analyte can be performed in a high throughput manner due to the scalability and the low cost of the detection. A software program was written to automate the calculation of g(r). The program inputs text files containing X,Y coordinate positions of each particle in each image. The software also takes into account such parameters such as pixel resolution of each image, size of particles, size of the image window, and desired resolution of g(r). g(r) can be resolved at high or low resolutions, however, it is preferred that g(r) be resolved at higher resolutions such as 0.04 because this has acceptable signal to noise ratio. If the resolution is lower, such as at 0.01 or lower resolutions, then there is likely too much noise. The program calculates and outputs the g(r) plot. Experiments were generally carried out at particle area fractions of $\phi \approx 0.15$-0.25, corresponding to ~7000 individual particles per image, where $\phi$ is the area of the window covered by particles, as opposed to the empty spaces between and around particles. Generally, about 5-10 independent images were averaged to generate g(r) from >$10^8$ measured pair distances.

The imaging of the field areas can be automated, as long as the pictures are taken consistently, with the only limitation being the speed of the automated camera, software and hardware. The g(r) plots may be generated fairly quickly so long as a sufficient number of particles are imaged over a sufficient time period.

It is further contemplated that the assay may be carried out with only such devices as a spectrophotometer or scanning plate reader that images or calculates light scattering in all wavelengths and spectra), to facilitate high throughput detection. The optical density of the particular particle population before the phase transition and at each phase transition is measured to capture the signature optical density reading. Upon addition and binding of an analyte to the derivatized particles, the plate can be scanned for whether or not a phase transition has been triggered.

Other factors that affect the detection assay include the hydration layers, coatings, and the charge of the materials that the assay is carried out in. It is presently contemplated that the detection assay is preferably carried out in a Corning COSTAR 96-well 3997 polystyrene plate or a comparable high throughput plate. The assay can be feasibly carried out in 96-, 384- or 1536-well plates.

Applications of the Technology

The colloidal particles described herein provide a sensitive, low-cost method of detecting analytes in any given solution. In the preferred embodiment, detection of the binding event to the ligand is used to detect pathogenic organisms, disease, toxins, contaminants, presence of a hormone, signaling molecule, antibody, cancer or a medical condition. In some embodiments, ligands are incorporated to detect a variety of pathogenic organisms including, but not limited to, sialic acid to detect HIV, *Chlamydia, Neisseria meningitidis, Streptococcus suis, Salmonella*, mumps, newcastle, and various viruses, including reovirus, Sendai virus, and myxovirus; and 9-OAC sialic acid to detect coronavirus, encephalomyelitis virus, and rotavirus; non-sialic acid glycoproteins to detect cytomegalovirus and measles virus; peptide sequences to hybridize to and identify the presence of Anthrax, CD4, vasoactive intestinal peptide, and peptide T to detect HIV; epidermal growth factor to detect vaccinia; acetylcholine receptor to detect rabies; Cd3 complement receptor to detect Epstein-Barr virus; β-adrenergic receptor to detect reovirus; ICAM-1, N-CAM, and myelin-associated glycoprotein MAb to detect rhinovirus; polio virus receptor to detect polio virus; fibroblast growth factor receptor to detect herpes virus; oligomannose to detect *Escherichia coli*; ganglioside $G_{M1}$ to detect *Neisseria meningitidis*; and antibodies to detect a broad variety of pathogens (e.g., *Neisseria gonorrhoeae, V. vulnificus, V. parahaemolyticus, V. cholerae*, and *V. alginolyticus*).

The membrane-derivatized colloidal system described herein has potential applications to a broad set of problems involving chemical events on cell membrane surfaces. These range from mapping ligand interactions with numerous cell surface proteins to detection of membrane-targeting bacterial toxins (e.g. botulism, cholera, anthrax, tetanus) and viruses. It should be realized that using natural biological membranes to coat the colloids allows a wide variety of analytes to be measured. Through the use of natural membranes, the assay can detect binding of analytes to ligands that are only found on natural membranes. As is known, many types of membrane bound ligands are not easily expressed in vitro, and thus the use of natural membranes provides many advantages.

Membrane-derivatized particles can be combined in heterogeneous mixtures or with live cells (e.g. rosetting), allowing the methodology outlined here to be applied to analysis of intermembrane receptor-ligand interactions. Implementation of the colloid assay is amenable to automated liquid handling and imaging systems. Detailed analysis of spatial distribution functions, such as the pair distribution studied here, enables characterization of subtle interactions, including those which may not produce qualitatively recognizable effects. At the same time, the use of membrane coatings on colloidal particles offers an extensive repertoire of chemical functionality, which may prove valuable in non-biological settings. It is anticipated that the general principles illustrated with lipid membranes in this work can be extended to other materials, such as the recently developed polymer vesicles.

Heterogeneous mixtures of particles can be used to examine interactions between membranes and/or membrane-associated ligands, or as a way of multiplexing. In this implementation, the particles could be individually identifiable with a label. The labels that can be used include, but are not limited to, fluorescent molecule doped into a particle material, fluorescent molecules doped into a membrane, semiconductor nanocrystals doped into particle material, etc. Strongly interacting particles of heterogeneous composition and functionality can be used as building blocks for assembly into complex, multi-functional, nanoscale structures that can be used analysis of more complicated systems.

Particles can be mixed with live cells to quantitatively observe cell activation and proliferation (e.g. cell rosetting), or examine cellular interactions and multiplexing by creating a readily observable, controllable interface which retains cell-like properties.

Particles can also be functionalized internally with materials such as fluorescent labels, semiconductor nanocrystals, nano-scale detection devices, or custom-designed nanocrystals or molecules.

Colloidal particles can be dispersed into many different environments such as the human body, areas where extreme toxics or caustics are present, or hard vacuum settings, to detect the presence of a contaminant for example. The binding event is allowed to occur, then the particles are collected, then subjected to conditions which allow the assay to be performed. Since the particles settle and only a finite number of particles having undergone the binding event must be collected, the particles can be dispersed in even such environments as a flowing body of water, e.g. a river. For example, the observable behavior and distribution of the particles after exposure to the river are compared with particles prior to casting in the river.

"Sensor" particles, exposed to the media under detection, can be moved through a plurality of background particles not exposed to the media. Phase data regarding the behavior of the particle can be elicited by observing the tracks of the relatively few "sensor" particles rather than looking at the overall spatial data of observing many particles in a finite location.

Example 1

Methods and Materials for Detection Assay using Silica Particles Derivatized with Ganglioside Doped Membranes Materials: Lipids were obtained from Avanti Polar Lipids. 1,2-Dimyristoleoyl-sn-glycero-3-phosphocholine (DMOPC), 1,2-dimyristoyl-sn-glycero-3-[phospho-L-serine] (sodium salt) (DMPS), and 1,2-dioleoyl-sn-glycero-3-ethylphosphocholine (DOEPC) were received in chloroform and stored at −20° C. for up to two weeks. Monosialoganglioside $G_{M1}$, bovine-ammonium salt ($G_{M1}$) was received from Matreya Inc. in powder form and dissolved in 2:1 chloroform/methanol to 1 mg/mL for storage at −20° C. Trisialoganglioside $G_{TIB}$, bovine brain ($G_{TIB}$) was received from Sigma in powder form and dissolved in 2:1 chloroform/methanol to 1 mg/mL for storage at −20° C. The fluorescent probe N-(Texas red sulfonyl)-1,2-dihexadecanoyl-sn-glycero-3-phosphoethanolamine, triethylammonium salt (Texas Red® DPPE) was purchased from Molecular Probes in powder form and dissolved in chloroform before use. Cholera toxin subunit B (CTB), FITC labeled, was purchased from Sigma, dissolved in 0.2×PBS to a concentration of 0.5 mg/mL and stored at 4° C. Unlabeled a-Bungarotoxin (BT) was purchased from Sigma, dissolved in 0.2×PBS to a concentration of 0.5 mg/mL and stored at 4° C. Tetanus toxin, c-fragment (TT), fluorescein labeled, was purchased from Calbiochem, reconstituted in sterile $H_20$ to a concentration of 0.1 mg/ml TT and 10 mM sodium phosphate buffer, and stored at 4° C. Bovine fetal calf serum (FCS) was purchased from Sigma, reconstituted in sterile $H_20$ and stored at 4° C. Unlabeled rabbit IgG fraction antibodies anti-Texas Red®, were purchased from Molecular Probes at a concentration of 1 mg/mL and stored at 4° C. 5 μm mean diameter silica glass microspheres were obtained from Bangs laboratories and stored at 4° C. under DI $H_20$.

Supported Membranes: Supported bilayers were formed by fusion of small unilamellar vesicles (SUV) onto clean glass microspheres. A lipid solution in chloroform was evaporated onto small round-bottom flasks and hydrated for an hour at 4° C. in 18.2 MΩ-cm water at ~3.3 mg/mL. The lipids were probe-sonicated to clarity in an ice-water bath and ultracentrifuged for 2 h at 160,000 g and 4° C. The supernatant was stored at 4° C. for up to one week. Glass surfaces were prepared for deposition by boiling at 250° C. in concentrated nitric acid followed by extensive rinsing. Bilayers were allowed to self-assemble on the particle surface by mixing equal amounts (100 μL) of spreading solution (1:1 SUV/PBS)

and particle solution together in a 1.5 mL centrifuge tube. Excess vesicles were removed by pelleting the particles via pulse-centrifugation and removal of the supernatant. 1 mL of 18.2 MΩ-cm water was then added to the pelleted particles and the entire mixture vortexed to allow resuspension.

Colloid Formation: Colloids were cast by diluting the particle suspension to desired concentrations and pipetting 200-300 µL of the suspension into Costar number 3997 96-well plates. The 96-well plates were left undisturbed for 15 minutes to allow even settling of the particles to the bottom of each well.

Imaging: Supported bilayer-coated particles were diluted to a working concentration and deposited onto Corning 96-well cell culture clusters for viewing. Particles were viewed at room temperature with a Nikon TE-300 inverted fluorescence microscope (Nikon, Japan) equipped with a mercury arc lamp for fluorescence and a 100 W halogen lamp for brightfield illumination. Images were recorded with a Roper Scientific CoolSnap HQ charge-coupled device camera (Roper Scientific CoolSnap HQ, USA). Images were acquired with SIMPLE PCI (Compix Inc., Cranberry Township, Pa.) and analyzed with METAMORPH (Universal Imaging Corporation, Cranberry Township, Pa.).

Data Analysis: To obtain Equation (1) discussed above, the pair distribution function is expressed as $$g(r) = n(r)/p(r),$$

where $n(r) = 2\eta(r)/(N(N-1)\delta r)$ is the actual relative density of particle pairs with separation distance r and $p(r) = 2(\pi XYr - 2(X+Y)r^2 + r^3)/(X^2Y^2)$ is the general probability density of finding a particle pair with separation distance r in a finite rectangular window of spatial dimensions X by Y. To obtain this expression for p(r), we solve the line integral $$p(r) = \int_Q p(r_x)p(r_y)dq,$$

where $p(r_x) = 2(X-r_x)/X^2$ and $p(r_y) = 2(Y-r_y)/Y^2$ are probability densities of finding a particle pair with $r_x$ and $r_y$ absolute projections of the separation vector r, respectively, and Q is the all-positive quarter of a circle.

At equilibrium, g(r) is physically related to the potential of mean force, w(r): $g(r) = e^{-w(r)/k_B T}$. In dilute systems, w(r) is equivalent to the pair interaction potential and thus provides a direct measure of the interaction energy. In more concentrated systems, w(r) includes effects due to neighboring particles. For quantitative comparison among samples, we isolate the first peak in g(r), which occurs at the particle diameter, and compute the corresponding effective interaction energy, $E_i$. This allows precise comparison among samples containing equal area fractions (φ) of particles and $E_i$ converges to the pure pair interaction energy at low coverage densities. Although equilibrium was required for $E_i$ to have meaningful units of energy, this was not a requirement for effective comparison. As long as each colloidal system was cast in an initially uncorrelated phase, nonequilibrium distribution measurements at defined time intervals could also be used for quantitative comparison. Independent measurements of g(r) were highly consistent. Standard deviations among $E_i$ values determined from separate colloidal preparations from the same starting materials were generally less than 0.1 $k_B T$.

Example 2

Detection Assay Using Silica Particles Derivatized with Ganglioside Doped Membranes Membrane-derivatized silica particles were dispersed, underwater, where they settled gravitationally onto the underlying substrate and form a two-dimensional colloid. The particles exhibited free lateral diffusion and the system behaved as an ergodic fluid. Brownian trajectories for a dilute collection of particles are illustrated in FIG. 2a. Particle diffusion coefficients were essentially independent of membrane composition; measurements ranged from 0.079 to 0.086 µm²/s for 5 µm diameter particles. These values are ~80% that predicted by the Stokes-Einstein relation for purely viscous drag, indicating a small contribution from drag on the underlying substrate. Depending on the strength of the interaction between membranes on the particle surfaces, dispersed (gas) or condensed (liquid or crystalline) phases of the colloid were observed. Particle mobility was retained in condensed phases (FIG. 2b). The mobility of individual particles, in both condensed and dispersed phases, defines the rate of system equilibration. The time-scale of particle condensation onto and evaporation from the condensed crystallites, seen in FIG. 2b, was rapid compared to that of our experiments (several minutes vs. more than half an hour). Additionally, the overall morphology and quantitative pair distribution functions of the phases remained constant, despite the interchange of individual particles. These observations suggest that the system is near equilibrium, at least over length-scales of several particle diameters.

The chemical composition of the lipid membrane was adjusted to modulate the pair interaction potential and is described below. Condensed phases, as seen in FIG. 2b, formed whenever the coating membrane was net neutral or negatively charged. In contrast, net positively charged membranes led to dispersed phases. The occurrence of multiple phases indicated that pair interaction energies poise the system near a phase transition. As such, small perturbations on the membrane surface are expected to induce significant changes in the macroscopic organization of the colloid. We observe this prediction by examining the effects of protein binding to membrane-associated ligands.

Several protein systems were studied: antibody binding membrane surface antigen and bacterial toxins, cholera (CTB) and tetanus (Ti), binding their respective membrane ligands, monosialoganglioside $G_{M1}$ and trisialoganglioside $G_{T1B}$. Particles coated with 9% phosphatidylserine/91% DMOPC membranes were prepared as described in Example 2.

The particles thus prepared formed condensed phases, consisting of short-lived crystallites, for all membrane surface ligands studied. In all cases, protein binding to membrane surfaces triggered a condensed to dispersed phase transition. FIG. 3 depicts a time sequence of a phase transition triggered by addition of protein at t=0 s. These experiments were performed with ~300 µl solution in ~5 mm round wells of a 96-well plate. Within 30 s of adding a drop of protein solution to the top of the well, uniform disruption of the condensed phase was discernable. Within 60 s, the colloid attained a dispersed distribution. Individual particle mobility is unaffected by protein binding. Exposure to a particular protein of interest triggered a phase transition from condensed to dispersed phase only when the appropriate cognate ligand was incorporated into the colloidal membrane. The physical presence of protein bound to the membrane surface increases the closest approach position between two membranes and, correspondingly, reduces the cumulative strength of the van der Waals attraction between particles.

Example 3

Detection using Derivatized Colloidal particles to Detect Cholera and Tetanus toxins Measurements of near equilibrium colloidal distributions over a range of protein and ligand concentrations were performed to explore the utility of the phase transition as a readout of protein binding on membrane surfaces. Antibody studies were performed using a monoclonal IgG antibody that binds the fluorescent membrane probe, Texas Red-DPPE.

Anti-Texas Red® rabbit IgG fraction antibodies were bound to Texas Red®-containing membranes by incubating a 20 µg/mL solution of the antibody with 1 mL of the particle solution for 45 minutes in the dark at room temperature, vortexing gently every 5 minutes. Antibodies were also bound to Texas Red®-containing membranes by adding antibody solution directly to the cast colloid in the 96-well plates. Bacterial toxins (CTB, TT, BT) were bound to membranes (containing either $G_{M1}$, $G_{T1B}$, or no ganglioside) by incubating the toxins at varying concentrations with particle solution for 50 minutes in the dark at room temperature, under continuous, gentle mixing.

Samples incubated with 20 µg/ml anti-Texas Red antibody exhibited a clear transition from condensed to dispersed phases for ligand surface concentrations $\geq 10"$ monolayer (FIG. 4a). This corresponds to ~10 ligand molecules on each membrane within the contact region where intermembrane separations were <10 nm (5 µM particles). For bacterial toxin binding studies, the ganglioside ligands $G_{T1B}$ or $G_{M1}$, were incorporated into membranes at a constant 0.5%. Incubation with TT triggered formation of a dispersed phase in the $G_{T1B}$-containing colloid while no effect was produced in the $G_{M1}$ colloid (FIG. 4b). Analogously, exposure to CTB triggered the transition to a dispersed phase in the $G_{M1}$ colloid without producing any effect on the $G_{T1B}$ colloid (FIG. 4c). Exposure to Bungarotoxin (1 µM) produced no effect in either colloid. The magnitude of the $r_0$ peak in the measured g(r) traces the surface concentration of bound protein.

Figure 4:
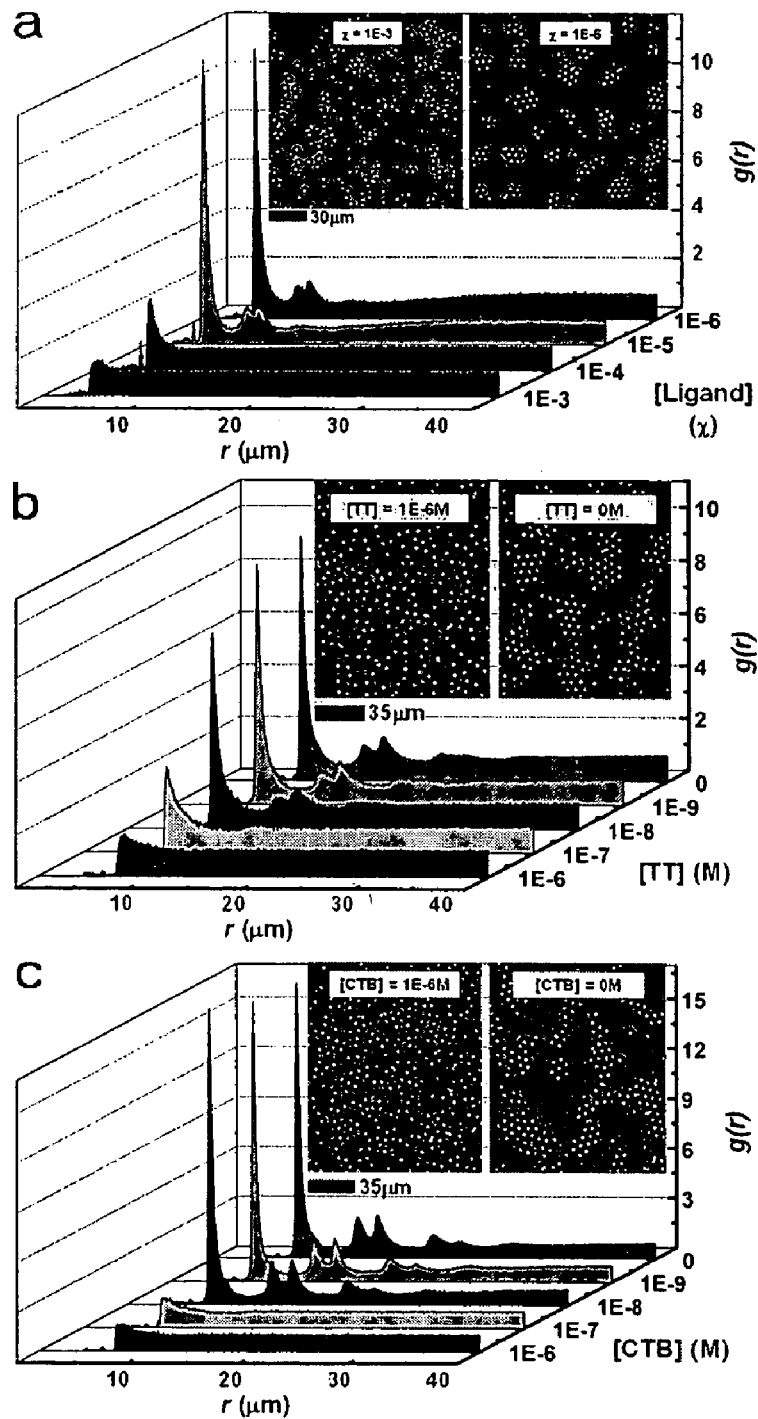
FIG. 4 shows a series of three-dimensional graphs illustrating the results of protein binding assays.

FIG. 4 illustrates results from a panel of membrane compositions with completely ionized charge densities ranging from $-1.43 \times 10^4$ to $7.15 \times 10^4$ e/µm$^2$ per membrane leaflet; actual surface charge densities are expected to be significantly lower due to incomplete ionization. Strongest interactions were seen for the particles derivatized with neutral membranes. This is consistent with the minimization of electrostatic repulsion expected between neutral surfaces. Away from neutrality, E, fell off rapidly for the positively charged membranes whereas only a slight, but consistent, reduction is observed as the membranes become negatively charged. The DMPS membranes used in the protein binding experiments ($-1.43 \times 10^5$ e/µm$^2$ at complete ionization) exhibited $E_i$ similar to that of the neutral membranes (~2 $k_BT$, see FIG. 3).

Figure 5A:
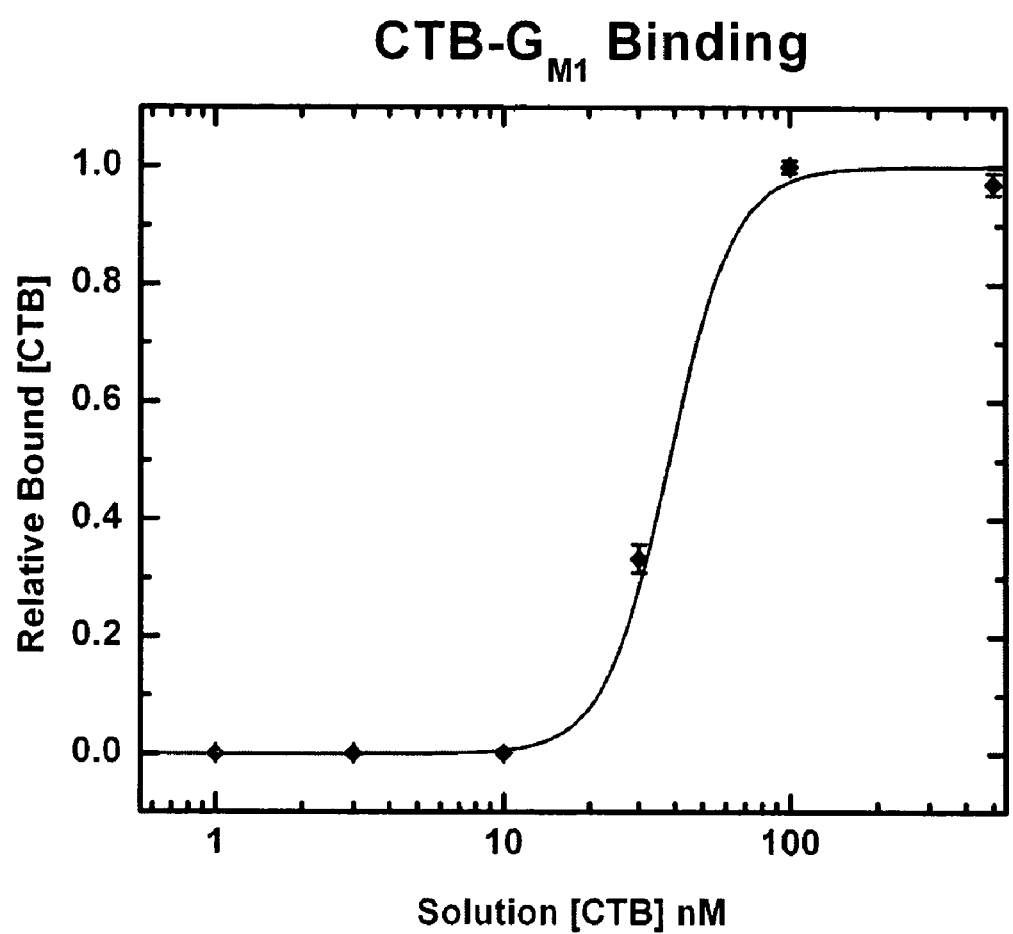
FIG. 5 is a set of line graphs showing parallel set of experiments on planar supported membranes. The graphs show the effective dissociation constants for CTB-$G_m$, (FIG. 5a) and TT-$G_{TTB}$ (FIG. 5b) binding were measured to be ~60 and ~41 nM, respectively.
FIG. 5c absence of binding when CTB is added to beads derivatized with membranes free of $G_{M1}$ and $G_{TTB}$.
FIG. 5d beads derivatized with $G_{M1}$-containing membranes detected binding of CTB, its natural ligand, but not α-Bungarotoxin (BT) or TT.
FIG. 5e beads derivatized with $G_{TTB}$-containing membranes detected binding of TT, its natural ligand, but not CTB or BT.
Figure 5B:
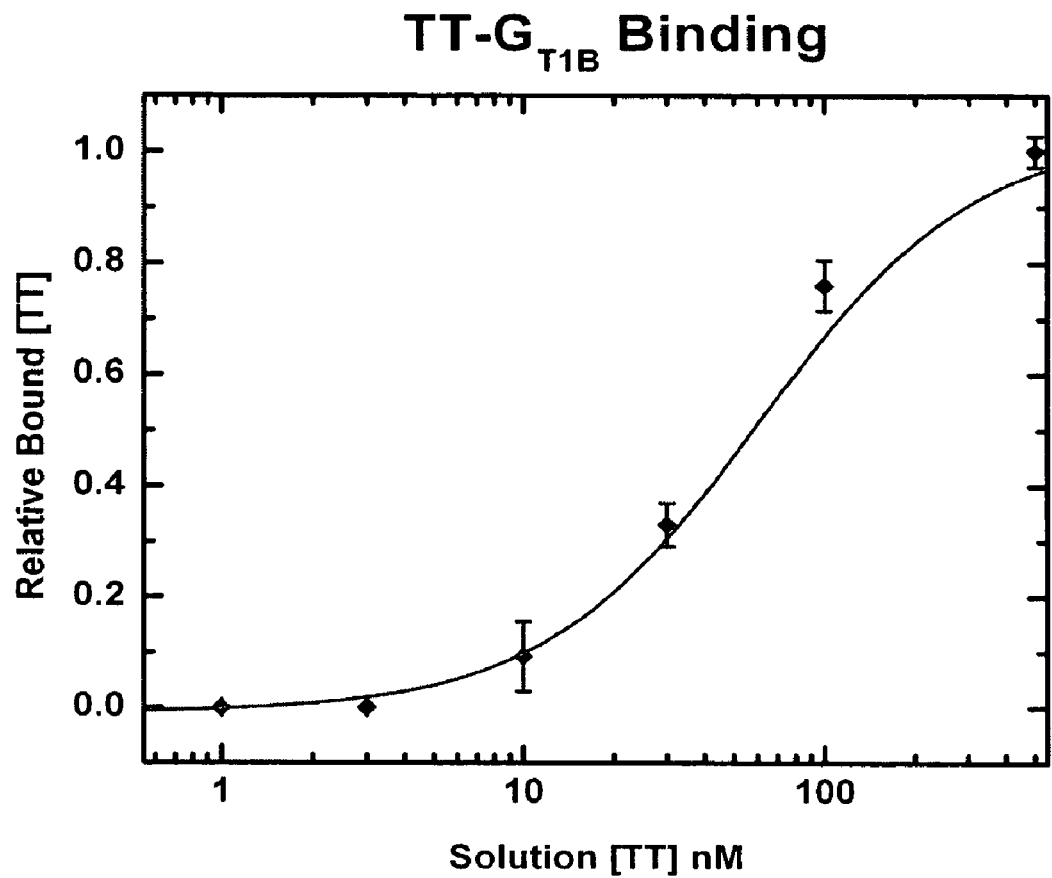

CTB-$G_{M1}$ and TT-$G_{T1B}$ binding was characterized by incubating planar supported membranes (formed by depositing SUV's onto glass coverslips) with varying concentrations of CTB and TT and monitoring fluorescence from either the FITC label (from CTB) or the fluoroescein label (from TT). Results indicate that CTB binds the 89% DMOPC/9% DMPS/1% $G_{M1}$/1% Texas Red DPPE membranes studied here with an effective dissociation constant of ~41 nM (see FIG. 5a). Since CTB-$G_{M1}$ binding is not monovalent, this is an approximate representation of the binding affinity. Results indicate that TT binds the 89% DMOPC/9% DMPS/1% $G_{T1B}$/1% Texas Red DPPE membranes studied here with an effective dissociation constant of ~60 nM (see FIG. 5B).

Realistic detection experiments were performed by mixing FCS (0.1%) and CTB (at a 100 nM concentration) in a sample of river water containing approximately 4 mg/mL of organic and inorganic components. The mixture was filtered with a 0.2 µm filter and incubated with 1 mL of the particle solution for 50 minutes in the dark at room temperature, continuously mixing gently. Excess soluble components were removed by rinsing the mixture with 18.2 M☐-cm water prior to casting the colloid.

Supporting Table 1 and FIGS. 5b, 5c, 5d and 5e contain results for a series of experiments designed to test the selectivity of the colloid detection scheme.

TABLE 1

| | $E_i$ values for several experiments | | | | | |
|---|---|---|---|---|---|---|
| Membrane Composition | No Toxin | CTB | TT | BT | FCS | FCS + CTB |
| 90% DMOPC, 9% DMPS, 1% Texas Red-DHPE | 2.83 ± 0.07 | 2.52 ± 0.09 | 2.61 ± 0.05 | 2.67 ± 0.10 | | 2.49 ± 0.05 |
| 89% DMOPC, 9% DMPS, 1% GM1, 1% Texas Red-DHPE | 2.78 ± 0.10 | 0.56 ± 0.12 | 2.63 ± 0.05 | 2.84 ± 0.02 | 3.24 ± 0.03 | 0.52 ± 0.07 |
| 89% DMOPC, 9% DMPS, 1% GT1B, 1% Texas Red-DHPE | 2.71 ± 0.09 | 2.47 ± 0.09 | 0.46 ± 0.07 | 2.71 ± 0.08 | | |

A value of Ei less than ~1 (shown in bold) in Table 1 indicates a strongly positive signal (toxin detection). Particles derivatized with membranes containing $G_{M1}$ (FIG. 5d), $G_{T1B}$ (FIG. 5e) or no ganglioside (FIG. 5c) were tested for binding affinity against CTB, TT and BT. The resulting colloidal distribution was evaluated in terms of an effective interaction energy, $E_i$. It was observed that in the absence of any type of toxin, particles derivatized with any of the three types of membranes had $E_i$ values greater than ~2. This value is representative of a condensed phase and is considered a negative signal. In the presence of a toxin and its specific target ($G_{M1}$-CTB, $G_{T1B}$-TT), the $E_i$ value for the colloid was less than ~1. This value is representative of a colloid in a dispersed phase and is considered a positive signal. In addition, specificity is explicitly shown with toxins in the presence of incorrect or nonexistent targets. Negative signals were obtained for the following systems: $G_{M1}$-TT, $G_{T1B}$-CTB, CTB and TT with no target, and BT with all three membrane types.

G(r) plots for all of this data are present in FIG. 5c. Insensitivity to a wider variety of potential targets was demonstrated by incubating 0.1% fetal calf serum (FCS) in the presence of a $G_{M1}$-containing membrane. The $E_i$ value of the resulting colloidal distribution was greater than ~2, indicative of a negative signal. Notice that when CTB was present and bound to the particles derivatized with the $G_{M1}$-containing membrane, the first peak in the g(r) plot was noticeably absent. And when the toxin to be detected was tetanus toxin, there was a noticeably absent peak in the g(r) plot for particles derivatized with $G_{TIB}$-containing membranes. Thus, the g(r) plots can qualitatively show that a toxin in solution has been detected and bound by the derivatized particles.

Example 4

Detection Using Heterogeneous Mixtures of Colloidal Particles

Two types of colloidal particles were made according to Example 1. One type was visualized as shaded, and the other visualized as white. Referring now to FIG. 6, the colloids were of the following composition: the shaded particles are silica microspheres of 6.8 µm diameter covered in a fluid lipid bilayer membrane (composition: 96% DMOPC, 3% DMPS, 1% Texas Red® DPPE). The white particles are nonporous, silica microspheres of 6.8 µm diameter covered in a fluid lipid bilayer membrane (composition: 98% DMOPC, 2% DOEPC, 1% 1,2-Dioleoyl-sn-Glycero-3-Phosphoethanolamine-N-(7-nitro-2-1,3-benzoxadiazol-4-yl, or NBD-PE). Particle location analysis is identical to that performed and outlined in Example 2.

Investigations of heterogeneous mixtures of colloids was accomplished by mixing dilute solutions of different colloids together at desired proportions. The resulting, heterogeneous colloid solution was then vortexed thoroughly and pipetted into a well of a 96 well plate to cast the colloid, as described above.

The analysis of determining the g(r) for the heterogeneous mixture of colloidal particles was performed as described below. For the binary colloid of FIG. 6a, φ=0.2 for the entire system of heterogeneous particles. The plot in FIG. 6b shows a characteristic representation of a heterogeneous g(r) plot.

Firstly, the evaluation of n(r), the actual relative density of particle pairs with separation distance r, for the four 'hetero-particle' cases:

n(r) of All Particles $$n_{ALL}(r) = \frac{2\eta_{ALL}(r)}{(N_S + N_W)(N_S + N_W - 1)\delta r}$$

$\eta_{ALL}(r)$ is the number of all particle pairs with separation distance $$r \pm \frac{\delta r}{2},$$

and $N_S$ and $N_W$ are total numbers of shaded and white particles, respectively. Since $N_S+N_W=N$ here, $n_{ALL}(r)$ is analogous to the original 'homo-particle' n(r).

n(r) of Shaded Particles $$n_S(r) = \frac{2\eta_S(r)}{N_S(N_S - 1)\delta r}$$

$\eta_S(r)$ is the number of shaded-shaded particle pairs with separation distance $$r \pm \frac{\delta r}{2}.$$

If we disregard white particles, which we can do here, $N_S=N$ and $n_S(r)$ is again analogous to the original 'homo-particle' n(r)

n(r) of White Particles

With the substitution S→W, $n_W(r)$ is analogous to $n_S(r)$ above.

n(r) of Shaded Particles Against White Particles (Heterogeneous Pair Correlation Function)

$$n_{SW}(r) = \frac{\eta_{SW}(r)}{N_S N_W \delta r}$$

$\eta_{SW}(r)$ is the number of particle hetero-pairs with separation distance $$r \pm \frac{\delta r}{2}.$$

This $n_{SW}(r)$ formula is the only one that really differs from the 'homo-particle' n(r) formula.

g(r) for the Four Cases

We use the original general definition formula:

$$g(r) = \frac{n(r)}{p(r)},$$

where p(r) is the probability density of finding a particle pair with separation distance r. While n(r) differed in the four discussed 'hetero-particle' cases, p(r) remains unchanged from the original 'homo-particle' p(r) and is:

$$p(r) = \frac{2}{X^2 Y^2}[\pi XYr - 2(X+Y)r^2 + r^3].$$

Combining the formulas above, we get the following:

$$g_{ALL}(r) = \frac{\eta_{ALL}(r)X^2Y^2}{(N_S + N_W)(N_S + N_W - 1)\delta r[\pi XYr - 2(X+Y)r^2 + r^3]}$$

$$g_S(r) = \frac{\eta_S(r)X^2Y^2}{N_S(N_S - 1)\delta r[\pi XYr - 2(X+Y)r^2 + r^3]}$$

$$g_W(r) = \frac{\eta_W(r)X^2Y^2}{N_W(N_W - 1)\delta r[\pi XYr - 2(X+Y)r^2 + r^3]}$$

$$g_{SW}(r) = \frac{\eta_{SW}(r)X^2Y^2}{2N_S N_W \delta r[\pi XYr - 2(X+Y)r^2 + r^3]}$$

Since p(r) is the same in all cases, the relationship between these four g(r) functions comes directly from comparison of their respective n(r) parts.

Figure 6A:
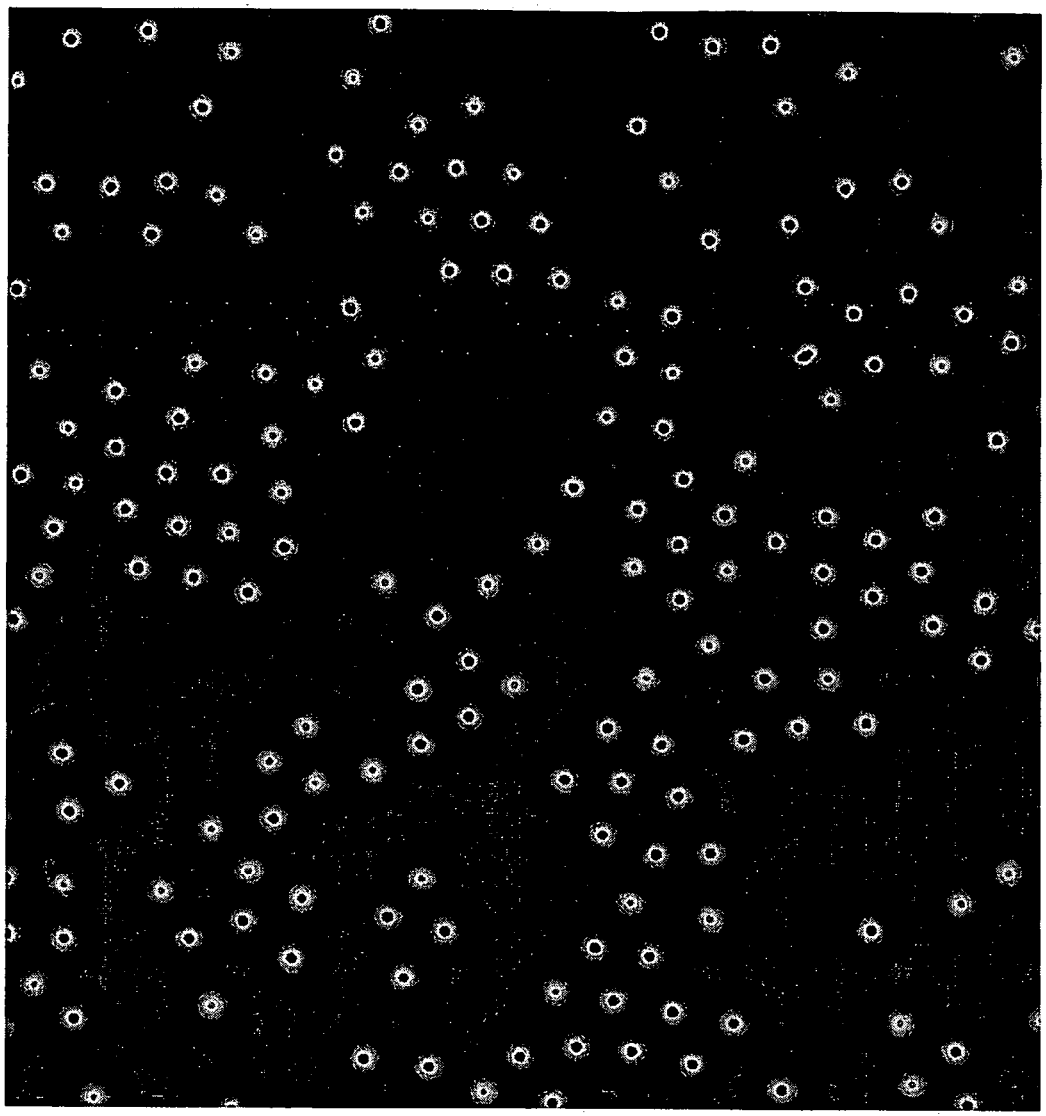
FIG. 6a is a photograph of microspheres in solution. The shaded particles are silica microspheres of 6.8 mm diameter covered in a fluid lipid bilayer membrane (composition: 96% DMOPC, 3% DMPS, 1% Texas Red^® DPPE). The particles colored in white are nonporous, silica microspheres of 6.8 mm diameter covered in a fluid lipid bilayer membrane (composition: 98% DMOPC, 2% DOEPC, 1% 1,2-Dioleoyl-sn-Glycero-3-Phosphoethanolamine-N-(7-nitro-2-1,3-benzoxadiazol-4-yl, or NBD-PE).
Figure 6B:
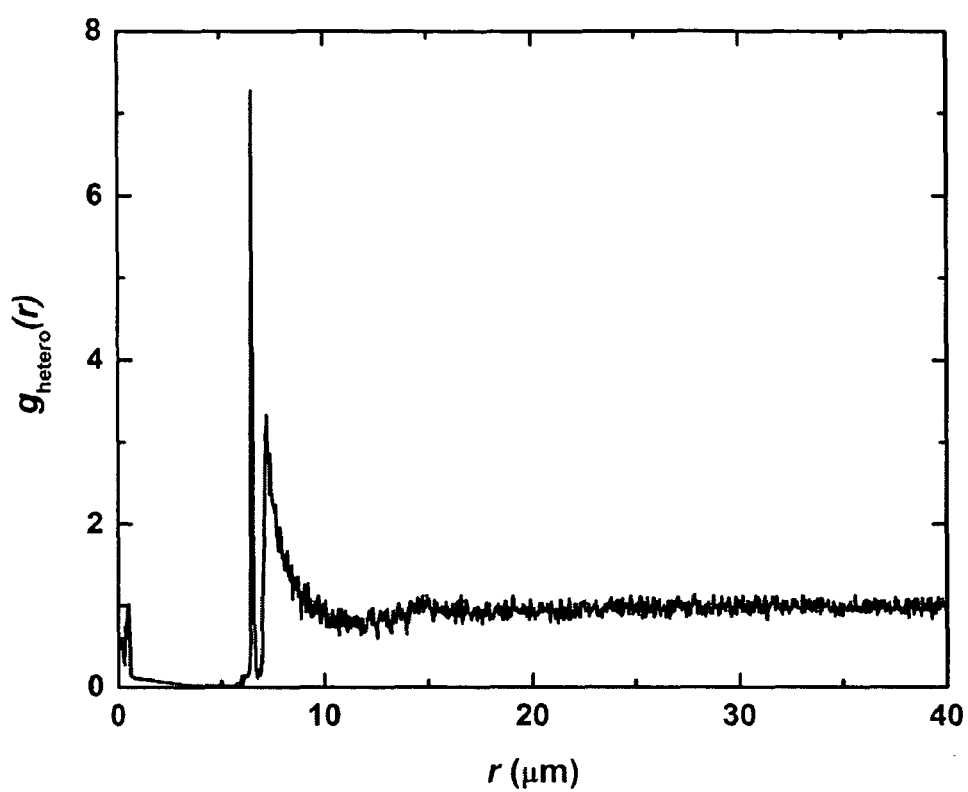
FIG. 6b shows a graph of a typical heterogeneous pair correlation function showing the relative density of shaded and white particle pairs in the sample.

A graphical representation of the relative density of shaded and white particle pairs depicted in the photograph of FIG. 6A is set forth in FIG. 6B. The first peak in this particular representation of the heterogeneous g(r) is extremely sharp, high, and occurs at exactly one bead diameter, indicating the presence of shaded and white particles that are in contact with each other. This is followed by a sharp drop in the value of the function, indicating an unfavorable energy region where absolutely no shaded and white particles interact. This is followed by further peaks which depict the relative density of shaded and white particle pairs with separation distance, r. It can be shown that changing the ionic strength of the solution that the colloid is in can change the width of the region where the heterogeneous g(r) indicates an unfavorable probability of two particles interacting. This effect can be utilized in situating heterogeneous mixtures of colloidal particles either closer to or farther from a phase transition point, thus making differences in phase behavior more sensitive.

Example 5

Detection using Colloidal particles

Realistic detection experiments were performed by mixing FCS (0.1%) and cholera toxin (CTB) (at a 100 nM concentration) in a sample of river water containing approximately 4 mg/mL of organic and inorganic components. The mixture was filtered with a 0.2 µm filter and incubated with 1 mL of the particle solution for 50 minutes in the dark at room temperature, continuously mixing gently. Excess soluble components were removed by rinsing the mixture with 18.2 MW-cm water prior to casting the colloid.

Upon analysis using the method of statistical analysis in Example 2, a positive signal from the system for detection of cholera was observed.

An alternative method is to disperse the particles with the cholera toxin ligand into the river, allow sufficient incubation time (say ~50 minutes), collect and isolate the particles from the river water, and then perform the analysis as outlined above.

Example 6

Alternate Method for Calculating the Pair Distribution Function

Alternate methods of calculating g(r) can be utilized to enhance computational efficiency. When observing a typical colloidal distribution, in the field of view, many particle pairs are separated by more than 40 μm. Since the pair-distribution becomes constant well before 40 μm, it is wasteful to calculate these pair distances and incorporate them into the histogram. Since the number of pair distances to be calculated scales as $N^2$ the number of particles in the image ($10^4$-$10^5$), the un-needed pair distances can slow down the calculation significantly. Since the particles are, at some level, hard spheres, n-th nearest-neighbors of a given bead are guaranteed to be more than 40 μm away from the center bead. For the 6.84 μm beads, 7th order nearest-neighbors are too far, but 6th order nearest-neighbors can still be in range. Thus, if one can find a way to only calculate pair-distances for 6th and lower order nearest-neighbor pairs, one can minimize the number of pair-distances which are calculated but irrelevant to the first 40 μm of the g(r).

To label the relevant pairs, an N×N matrix is used. If bead i and bead j are 6th or lower order nearest-neighbors, there should be a 1 indicating their pair distance should be calculated and incorporated into the histogram. If they are higher-order nearest neighbors, there should be a zero. The above-described approach is equivalent to filling this matrix with 1's. Typically, less than 8% of the particle pairs relevant to the 40 μm g(r).

To obtain this matrix, a matrix labeling first order nearest-neighbor pairs is calculated. For convenience, let the first order nearest-neighbor matrix be called: G. This matrix, G, is a mathematical representation of the network one would obtain by drawing line segments connecting the centers of nearest-neighbor beads. If there is a line segment connecting bead i to bead j, there will be a 1 in cell (i,j) of G. So G has a direct geometric meaning (it tells you how to connect the dots). The nearest neighbor network can be calculated very quickly using a method called Delaunay Triangulation. This method is important for applications computational geometry.

In graph theory, the matrix G has another meaning as well. G can operate on the network to give more complicated networks containing high-order nearest neighbor pairs. So $G^2$ is the network of 2nd and lower nearest neighbors. $G^6$ is the network of 6th and lower order nearest neighbors. So the algorithm works as follows:

given set of (x,y) pairs describing the position of each bead
1) Calculate G using Delaunay triangularion
2) Calculate $G^6$
3) for every 1 in the upper-triangular part of G
a) calculate the pair distance
b) incorporate the pair distance into the histogram
4) normalize the histogram.

Example 7

Protein Detection Using Native Cell Membranes

Detection of membrane-bound proteins was performed using "crude" membrane extracts obtained directly from native cells to coat particles. Specifically, 6.8 mm mean diameter silica microbeads were coated with vesicles prepared directly from the natural cell membrane of human erythrocyte cells. Natural cell membranes are membranes that are taken from a living cell. It was then shown that the act of binding of an antibody to the native, membrane-bound, intracellular protein present in the erythrocyte membrane, Band III, was sufficient to trigger a phase transition.

Red blood cell ghosts were created using the methods of Kaufmann et al. (Kaufmann, S. & Tanaka, M. Cell Adhesion onto Highly Curved Surfaces: One-Step Immobilization of Human Erythrocyte Membranes on Silica Beads. ChemPhysChem 4, 699-704 (2003)). The resulting cells were then probe-sonicated in 5 mM Tris buffer, pH 8.0 at 25 W for 90 seconds, (5 second pulses with 1 second intervals) in an ice water bath to produce small unilamellar vesicles (SUV's). The SUV's in buffer were ultracentrifuged for 2 hours at 160,000 g and 4° C. The supernatant was stored at 4° C. in 5 mM Tris buffer, pH 8.0 for up to 48 hours. Bilayers were allowed to self-assemble on the microbead surface by mixing equal amounts (100 mL) of spreading solution (1:1 SUV/1× Tris Buffered Saline, pH 7.4) and microbead suspension (10% solids in deionized water) together in a 1.5 mL centrifuge tube. Excess vesicles were removed by pulse centrifugation and removal of the supernatant. 1 mL of 5 mM Tris buffer, pH 8.0 was then added to the microbeads and the entire mixture was vortexed to allow the microbeads to resuspend.

Prior to antibody staining, the beads were incubated in BSA (15 mg/mL) for 1 hour to prevent nonspecific adsorption of antibodies. The intracellular Band III domain was then identified using a monoclonal mouse IgG antibody in physiological buffer. The bound mouse IgG was then detected by a Texas Red-labeled polyclonal goat anti-mouse antibody. The incubation time for each antibody was 30 minutes. The beads were rinsed thoroughly with 18.2MΩ-cm water, diluted to an acceptable working concentration, cast into a 96 well plate and allowed to settle by gravity. The microbeads were viewed at room temperature with a Nikon TE-300 inverted fluorescence microscope equipped with a mercury arc lamp for fluorescence and a 100 W halogen lamp for brightfield illumination. Images were recorded with a Roper Scientific CoolSnap HQ charge-coupled device camera.

The result of this experiment were analogous to the results of the antibody assay performed in Example 2, as shown above. In this case, binding of the antibody was sufficient to cause the colloid to undergo a phase transition from the condensed to the dispersed phase.

It should be realized that this experiment could be modified to perform proteomic analyses similar, but simpler than, those currently available (ELISA, etc.), as no secondary antibodies or complex light-detection equipment is required. Model cells lines such as HEK and CHO cells, that are well-characterized genetically, can be transformed to display any number of membrane-bound/associated analytes. In addition, native cells displaying naturally-occurring analytes could also be used, and may even be more appropriate in cases where the engineering of model cells is not feasible or appropriate (proteins that are difficult to engineer for expression, those that are found to be naturally occurring at high concentrations in native cells, etc).

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

We claim:

1. A method for detecting an analyte in a sample, comprising:
   providing a suspension of colloidal particles, wherein said particles are associated with a ligand that binds to said analyte, and wherein said colloidal particles are near a dynamical phase transition state;
   contacting said suspension with said sample; and
   determining whether said colloidal particles transition from a first phase to a second phase, wherein such transition is indicative of said analyte being present in said sample.

2. The method of claim 1, wherein said colloidal particles comprise a lipid layer.

3. The method of claim 2, wherein said lipid layer comprises a lipid bilayer.

4. The method of claim 3, wherein said lipid bilayer comprises a natural cell membrane.

5. The method of claim 3, wherein said lipid bilayer comprises an artificial cell membrane.

6. The method of claim 1, wherein said colloidal particles are covalently linked to said ligand.

7. The method of claim 1, wherein said ligand is non-covalently linked to said colloidal particles.

8. The method of claim 1, wherein said ligand is interspersed within a lipid layer on said colloidal particles.

9. The method of claim 1, wherein said colloidal particles have a net negative charge or a net neutral charge.

10. The method of claim 1, wherein said analyte is selected from the group consisting of: a protein, a nucleic acid, an antibody, an antigen, a receptor, a virus, and a bacteria.

11. The method of claim 1, wherein determining whether said colloidal particles transition from a first phase to a second phase comprises measuring the distances between centers of said colloidal particles in said suspension.

12. The method of claim 1, wherein said colloidal particles are between 1 µm and 10 µm.

13. The method of claim 1, wherein said first phase is a condensed phase and said second phase is a dispersed phase.

14. The method of claim 1, wherein said first phase is a dispersed phase and said second phase is a condensed phase.

15. The method of claim 1, wherein said suspension of colloidal particles comprises a first population of colloidal particles and a second population of colloidal particles.

16. The method of claim 15, wherein said first population comprises colloidal particles that are larger than the colloidal particles in said second population.

17. The method of claim 15, wherein said first population comprises colloidal particles that are labeled differently than the colloidal particles in said second population.

18. An assay system for detecting the binding of an analyte to a ligand, comprising:
   a suspension of colloidal particles, wherein each colloidal particle comprises a single central particle associated with more than one copy of a ligand specific for said analyte; and wherein said colloidal particles are near a dynamical phase transition state and comprise a lipid layer; and
   a device configured to determine if said colloidal particles transition from a first phase to a second phase when contacted by said analyte, wherein such transition is indicative of said analyte being bound to said ligand.

19. The assay system of claim 18, wherein said suspension of colloidal particles comprises a first population of colloidal particles and a second population of colloidal particles.

20. The assay system of claim 19, wherein said first population comprises colloidal particles that are larger than the colloidal particles in said second population.

21. The assay system of claim 19, wherein said first population comprises colloidal particles that are labeled differently than the colloidal particles in said second population.

22. The assay system of claim 18, wherein said lipid layer comprises a natural cell membrane.

23. The assay system of claim 18, wherein said colloidal particles are covalently linked to said ligand.

24. The assay system of claim 18, wherein said ligand is non-covalently linked to said colloidal particles.

25. The assay system of claim 18, wherein said first phase is a condensed phase and said second phase is a dispersed phase.

26. The assay system of claim 18, wherein said first phase is a dispersed phase and said second phase is a condensed phase.

27. An assay system for detecting the binding of an analyte to a ligand, comprising:
   a suspension of colloidal particles, wherein said particles are coated with a lipid, layer, and wherein said particles are near a dynamical phase transition state;
   a ligand associated with said lipid layer, wherein said ligand is specific for said analyte; and
   means for detecting if said colloidal particles transition from a first phase to a second phase when contacted by said analyte, wherein such transition is indicative of said analyte being bound to said ligand.

28. The assay system of claim 27, wherein said means for detecting comprises a microscope.

29. The assay system of claim 27, wherein said means for detecting comprises a fluorescence detector.

30. The assay system of claim 27, wherein said lipid layer comprises a natural cell membrane.

31. The assay system of claim 27, wherein said ligand is non-covalently linked to said lipid layer.

32. The assay system of claim 18, wherein said single central particle comprises silica.

33. The assay system of claim 32, wherein said single central particle is a silica microsphere or microbead.

34. The assay system of claim 18, wherein said single central particle comprises a metal.

35. The assay system of claim 27, wherein each colloidal particle comprises a single central particle associated with more than one copy of said ligand; and wherein said lipid layer coats said single central particle.

36. The assay system of claim 35, wherein said single central particle is a silica microsphere or microbead.

37. The assay system of claim 18, wherein the lipid layer is a bilayer.

38. The assay system of claim 18, wherein the lipid layer is a monolayer.

39. The assay system of claim 18, wherein the lipid layer comprises 1,2-dimyristoleoyl-sn-glycero-3-phosphocholine (DMOPC).

40. The assay system of claim 39, wherein the lipid layer comprises at least about 90% 1,2-dimyristoleoyl-sn-glycero-3-phsphocholine DMOPC.

41. The assay system of claim 18, wherein the lipid layer comprises 1,2-dimyristoyl-sn-glycero-3 [phosphor-L-serine] (DMPS).

42. The assay system of claim 18, wherein the lipid layer comprises 1,2-dioleoyl-sn-glycero-3-ethylphosphocholine (DOEPC).

43. The assay system of claim 18, wherein the lipid layer comprises 1,2-dihexadecanoyl-sn-glycero-3-phosphoethanolamine (DPPE).

44. The assay system of claim 27, wherein the lipid layer is a bilayer.

45. The assay system of claim 27, wherein the lipid layer is a monolayer.

46. The assay system of claim 27, wherein the lipid layer comprises 1,2-dimyristoleoyl-sn-glycero-3-phsphocholine (DMOPC).

47. The assay system of claim 46, wherein the lipid layer comprises at least about 90% 1,2-dimyristoleoyl-sn-glycero-3-phsphocholine DMOPC.

48. The assay system of claim 27, wherein the lipid layer comprises 1,2-dimyristoyl-sn-glycero-3 [phosphor-L-serine] (DMPS).

49. The assay system of claim 27, wherein the lipid layer comprises 1,2-dioleoyl-sn-glycero-3-ethylphosphocholine (DOEPC).

50. The assay system of claim 27, wherein the lipid layer comprises 1,2-dihexadecanoyl-sn-glycero-3-phosphoethanolamine (DPPE).

* * * * *